(12) United States Patent
Sabroe et al.

(10) Patent No.: US 8,362,287 B2
(45) Date of Patent: Jan. 29, 2013

(54) STEREOSELECTIVE SYNTHESIS OF VITAMIN D ANALOGUES

(75) Inventors: Thomas Peter Sabroe, Virum (DK); Martin John Calverley, Herlev (DK)

(73) Assignee: Leo Pharma A/S, Ballerup (DK)

( * ) Notice: Subject to any disclaimer, the term of this patent is extended or adjusted under 35 U.S.C. 154(b) by 1181 days.

(21) Appl. No.: 10/549,315

(22) PCT Filed: Mar. 10, 2005

(86) PCT No.: PCT/DK2005/000161
§ 371 (c)(1),
(2), (4) Date: Sep. 28, 2006

(87) PCT Pub. No.: WO2005/087719
PCT Pub. Date: Sep. 22, 2005

(65) Prior Publication Data
US 2007/0027333 A1    Feb. 1, 2007

Related U.S. Application Data

(60) Provisional application No. 60/553,962, filed on Mar. 18, 2004.

(30) Foreign Application Priority Data

Mar. 22, 2004 (DK) .................................. 2004 00454

(51) Int. Cl.
*C07C 401/00* (2006.01)
*C07D 333/64* (2006.01)
*A61K 31/593* (2006.01)

(52) U.S. Cl. ........................... 552/653; 514/167; 549/53

(58) Field of Classification Search .................. 514/167; 552/652; 549/53
See application file for complete search history.

(56) References Cited

U.S. PATENT DOCUMENTS

| 4,866,048 A * | 9/1989 | Calverley et al. ............. 514/167 |
| 5,763,426 A * | 6/1998 | Hansen et al. ................. 514/167 |
| 6,531,460 B1 | 3/2003 | Takenouchi et al. |
| 7,205,420 B2 * | 4/2007 | Shapiro et al. ................ 552/653 |
| 7,351,869 B2 * | 4/2008 | Schwartz et al. ............. 568/828 |
| 7,700,580 B2 * | 4/2010 | Kutner et al. ................. 514/167 |

FOREIGN PATENT DOCUMENTS

| WO | WO-87/00834 A | 2/1987 |
| WO | WO98/24800 | 6/1998 |
| WO | WO 03/060094 A2 | 7/2003 |

OTHER PUBLICATIONS

Martin J. Calverley, The Seleno-Acetal Route to Side-Chain-Modified 1α Hydroxy-Vitamin D Analogues: Stereoselective Synthesis of the New 22Z Isomer of MC 903 (Calcipotriol), SYNLETT 1990; p. 157-159.

Ishiguro et al, Stereoselective ntroduction of Hydroxy-groups into the 24-, 25-, and 26-Positions of the Cholesterol Side Chain, J.C.S. Chem. Comm., 115-117, 1981, p. 115-117.

Calverley, Martin J., "Synthesis of MC 903, A Biologically Active Vitamin D Metabolite Analogue," *Tetrahedron* vol. 43, No. 20. pp. 4609 to 4619, 1987, G.B.

Calverley et al., 1α, 24S-Dihydroxy-26,27-Cyclo-22-YNE-Vitamin $D_3$: The Side Chain Triple Bond Analogue of MC 903 (Calcipotriol), *Bioorganic & Medicinal Chemistry Letters*, vol. 3, No. 9, pp. 1841-1844, 1993.

Sabroe, Thomas Peter, Chirale allylalkoholer ved asymmetrisk induktion, (master's thesis); Danmarks Tekniske Universitet, Institut for Ogranisk Kemi, 1997; and Declaration containing partial English Translation.

Ashcroft et al., "Systematic review of comparative efficacy and tolerability of calcipotriol in treating chronic plaque psoriasis", Papers, BMJ, vol. 320, 2000, pp. 963-967.

Castelijns et al., Proliferation is the Main Epidermal Target in the Treatment of Psoriatic Plaques with Once Daily Application of Tacalcitol Ointment, Acta Derm Venereol (Stockh), 1999, 79, pp. 111-114.

* cited by examiner

*Primary Examiner* — Sabiha Qazi
(74) *Attorney, Agent, or Firm* — Birch Stewart Kolasch & Birch, LLP

(57) ABSTRACT

The present invention relates to intermediates useful for the synthesis of calcipotriol or calcipotriol monohydrate, to methods of producing said intermediates, and to methods of stereoselectively reducing said intermediates.

17 Claims, No Drawings

STEREOSELECTIVE SYNTHESIS OF VITAMIN D ANALOGUES

This Non-provisional application claims priority under 35 U.S.C. §119(e) on U.S. Provisional Application No(s). 60/553,962 filed on Mar. 18, 2004 and under 35 U.S.C. §119(a) on Patent Application No(s). PA 2004 00454 filed in Denmark on Mar. 22, 2004, the entire contents of which are hereby incorporated by reference.

FIELD OF THE INVENTION

The present invention relates to methods of producing calcipotriol {(5Z,7E,22E,24S)-24-cyclopropyl-9,10-secochola-5,7,10(19),22-tetraene-1α-3β-24-triol} or calcipotriol monohydrate by stereoselective reduction. The present invention further provides novel intermediates and methods for the synthesis of the intermediates useful for producing calcipotriol or calcipotriol monohydrate.

BACKGROUND OF THE INVENTION

Calcipotriol or calcipotriene (structure I) [CAS 112965-21-6] shows a strong activity in inhibiting undesirable proliferation of epidermal keratinocytes [F. A. C. M. Castelijins, Gerritsen, I. M. J. J. van Vlijmen-Willems, P. J. van Erp, P. C. M. van de Kerkhof; Acta Derm. Venereol. 79, 11, 1999]. The efficiency of calcipotriol and calcipotriol monohydrate (II) in the treatment of psoriasis was shown in a number of clinical trials [D. M. Ashcroft et al.; Brit. Med. J. 320, 963-67, 2000] and calcipotriol is currently used in several commercial drug formulations.

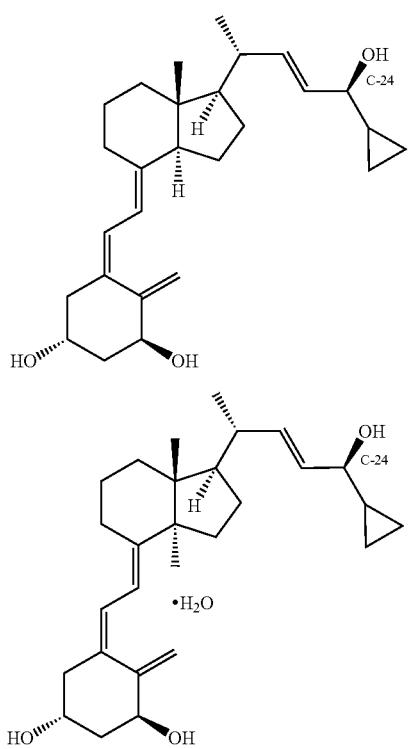

In the preparation of calcipotriol, the specific stereochemistry for the hydroxyl group at C-24 is necessary for full expression of the biological activity. Under current methodology, the required stereochemistry is introduced by one of the following methods:

(i) non-diastereoselective reduction of C-24 keto-trienes followed by the separation of diastereomeric mixtures of the C-24 hydroxyl epimers obtained via chromatography (WO 87/00834 & M. J. Calverley; Tetrahedron, 43 (20), 4609-19, 1987);

(ii) attachment of an enantiopure C-24-hydroxyl-carrying side chain to the vitamin D skeleton (M. J. Calverley, Synlett, 157-59, 1990);

(iii) selective enzymatic esterification of one of C-24 hydroxyl epimers followed by chromatographic separation (WO 03/060094).

The non-diastereoselective reduction of C-24 keto-trienes followed by chromatographic separation of the epimeric mixture (i) is the most widely practiced procedure for obtaining the desired epimer. This reduction process yields mainly the undesired C-24 epimeric alcohol (typically about 60% of the unwanted 24-R epimer) and it is difficult to separate the desired S-epimer from such a mixture by chromatography on a production scale.

The stereoselective synthesis (ii) is still an unfavourable process for scale up due to its multi step nature and cost and due to the fact that toxic intermediates are used. The enzymatic esterification process (iii) has the disadvantage, apart from the high cost of the enzymes employed, that it introduces, depending on the selectivity of the enzyme, 1-2 additional reaction steps which adds even further costs to the process.

The stereoselective reduction of C-24 ketones directly to the desired C-24 hydroxyl epimers has for example been described for cholesterol derivatives in WO 98/24800 and by M. Ishiguro et al., J. C. S. Chem. Comm., 115-117, 1981. The stereoselective reduction of a side chain triple bond analogue of calcipotriol with unprotected triene system using S-alpine borane has been described by M. J. Calverly et al. in Bioorg. Med. Chem. Lett., 1841-1844, 3(9), 1993.

A major technical problem of using stereoselective reduction methods for the synthesis of calcipotriol stems from the fact that the unsaturated triene system of hitherto known intermediates for the synthesis of calcipotriol are chemically labile, such as towards Lewis acidic conditions, that they are relatively easily oxidised, and that they are usually not compatible with the typical reduction reaction conditions employed. This results in reduced yields, impure products and tedious work-up procedures, especially on large-scale.

It is an object of this invention to provide an alternative process for the synthesis of calcipotriol, which may overcome one or more of the various problems and disadvantages described above.

The present invention provides a novel process to produce diastereomerically enriched C-24 hydroxyl epimers of calcipotriol derivatives using a novel synthetic pathway comprising a stereoselective reduction step. The present invention further provides novel chemically more stable intermediates where the labile triene system is protected as sulphur dioxide adduct. By producing diastereomerically enriched C-24 hydroxyl epimers of calcipotriol derivatives the yield and the efficacy of the subsequent separation of the desired C-24 S-hydroxyl epimer may be greatly improved.

SUMMARY OF THE INVENTION

It has surprisingly been found that compounds of general structure III,

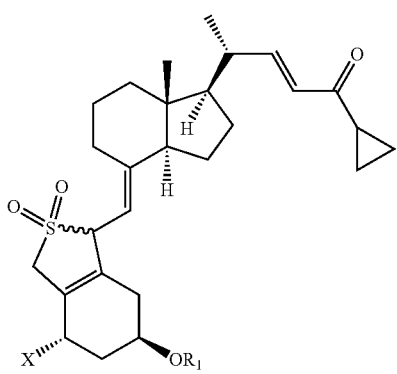

III wherein X represents either hydrogen or $OR_2$,
and wherein $R_1$ and $R_2$ may be the same or different and represent hydrogen, or a hydroxy protecting group,
in an inert solvent with a reducing agent or with a reducing agent in the presence of a chiral auxiliary,
to give a mixture of compounds of general structure IVa and IVb,

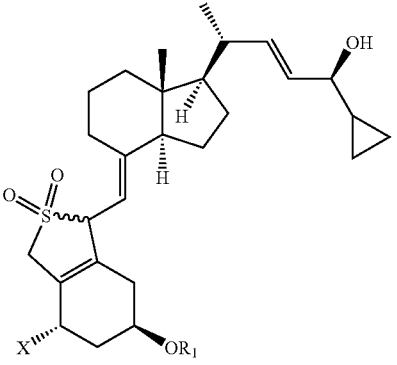

IVa

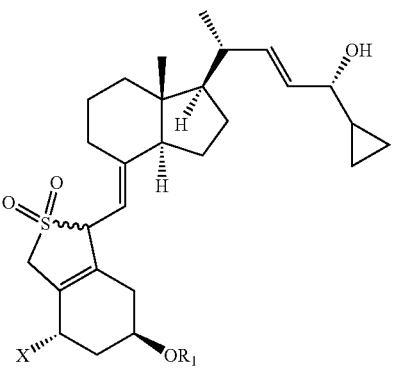

IVb which is enriched with IVa, wherein X, $R_1$, and $R_2$ are as defined above.

In a first aspect, this invention relates to a method for producing calcipotriol {(5Z,7E,22E,24S)-24-cyclopropyl-9,10-secochola-5,7,10(19),22-tetraene-1α-3β-24-triol} or calcipotriol monohydrate comprising the steps of:

(a) reducing a compound of general structure III,
wherein X represents $OR_2$,
and wherein $R_1$ and $R_2$ may be the same or different and represent hydrogen or a hydroxy protecting group,
in an inert solvent with a reducing agent or with a reducing agent in the presence of a chiral auxiliary,
to give a mixture of compounds of general structure IVa and IVb, which is enriched with IVa,
wherein X, $R_1$ and $R_2$ are as defined above;
(b) reacting the mixture of compounds of general structure IVa and IVb, which is enriched with IVa, in the presence of a base to give a mixture of compounds of general structure Va and Vb, which is enriched with Va,

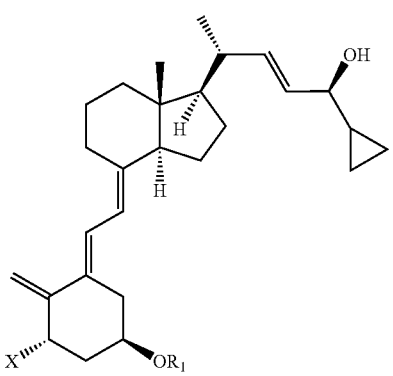

Va

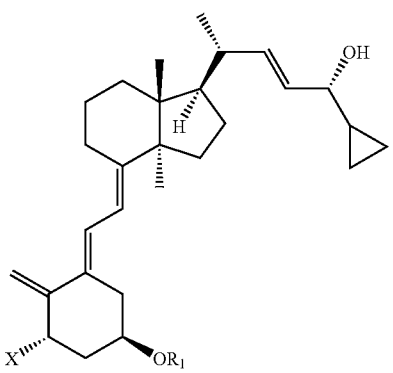

Vb wherein X, $R_1$ and $R_2$ are as defined above;
(c) separating the compound of general structure Va from the mixture of compounds of general structure Va and Vb which is enriched with Va, wherein X, $R_1$ and $R_2$ are as defined above;
(d) isomerising the compound of general structure Va to the compound of general structure VIa,

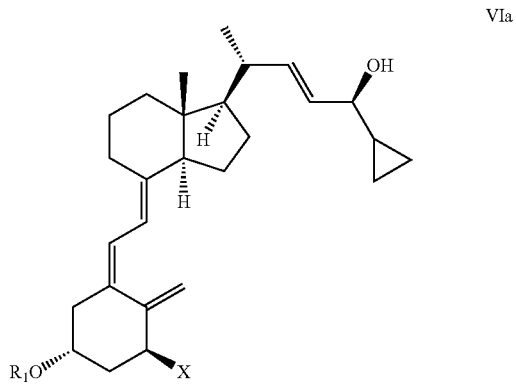

VIa wherein X, $R_1$ and $R_2$ are as defined above; and (e) when $R_1$ and/or $R_2$ are not hydrogen, removing the hydroxy protecting group(s) $R_1$ and/or $R_2$ of the compound of general structure VIa to generate calcipotriol or calcipotriol monohydrate.

In a further aspect, this invention relates to a method for producing calcipotriol or calcipotriol monohydrate comprising steps (a)-(b) above and further comprising the steps of:
(f) isomerising the mixture of compounds of general structure Va and Vb, wherein X, $R_1$ and $R_2$ are as defined in claim 2, which is enriched with Va, to a mixture of compounds of general structure VIa and VIb, which is enriched with VIa,

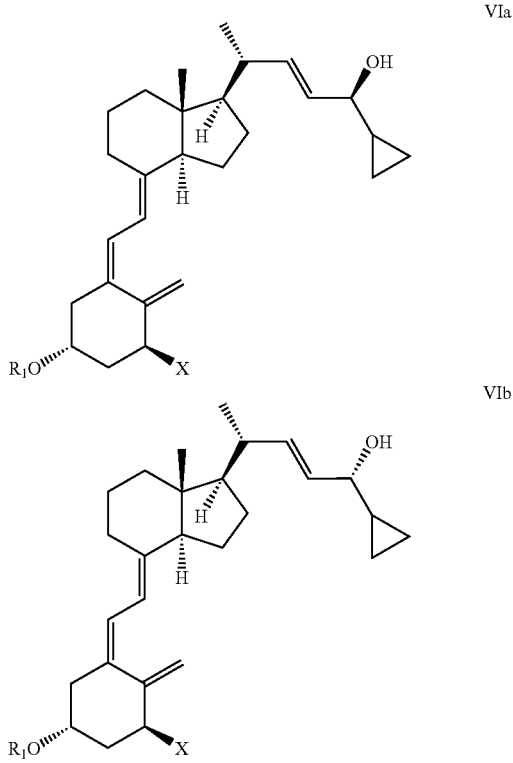

wherein X, $R_1$ and $R_2$ are as defined above;
(g) separating the compound of general structure VIa from the mixture of compounds of general structure VIa and VIb which is enriched with VIa, wherein X, $R_1$ and $R_2$ are as defined above;
(h) when $R_1$ and/or $R_2$ are not hydrogen, removing the hydroxy protecting group(s) $R_1$ and/or $R_2$ of the compound of general structure VIa to generate calcipotriol or calcipotriol monohydrate.

In a still further aspect, this invention relates to a method for producing calcipotriol {(5Z,7E,22E,24S)-24-cyclopropyl-9,10-secochola-5,7,10(19),22-tetraene-1α-3β-24-triol} or calcipotriol monohydrate comprising the steps of:
(j) reducing a compound of general structure III,
wherein X represents hydrogen,
and wherein $R_1$ represents hydrogen or a hydroxy protecting group,
in an inert solvent with a reducing agent or with a reducing agent in the presence of a chiral auxiliary,
to give a mixture of compounds of general structure IVa and IVb, which is enriched with IVa,
wherein X and $R_1$ are as defined above;
(k) reacting the mixture of compounds of general structure IVa and IVb, which is enriched with IVa, in the presence of a base to give a mixture of compounds of general structure Va and Vb, which is enriched with Va,
wherein X and $R_1$ are as defined above;
(l) separating the compound of general structure Va from the mixture of compounds of general structure Va and Vb which is enriched with Va, wherein X and $R_1$ are as defined above;
(m) hydroxylating the compound of general structure Va with a suitable hydroxylating agent, wherein X and $R_1$ are as defined above to give a compound of general structure Va, wherein X represents $OR_2$ and $R_2$ represents hydrogen, and wherein $R_1$ is as defined above;
(o) isomerising the compound of general structure Va to the compound of general structure VIa,
wherein X, $R_1$ and $R_2$ are as defined above; and
(p) when $R_1$ is not hydrogen, removing the hydroxy protecting group $R_1$ of the compound of general structure VIa to generate calcipotriol or calcipotriol monohydrate.

In a still further aspect, this invention relates to a method for producing calcipotriol or calcipotriol monohydrate comprising steps (j)-(l) of claim 4 and further comprising the steps of:
(q) protecting the C-24 hydroxy group of the compound of general structure Va, wherein X represents hydrogen, and wherein $R_1$ represents hydrogen or a hydroxy protecting group, with a hydroxy protecting group;
(r) hydroxylating the C-24 hydroxy protected compound of general structure Va with a suitable hydroxylating agent, wherein X and $R_1$ are as defined above to give a C-24 hydroxy protected compound of general structure Va, wherein X represents $OR_2$ and $R_2$ represents hydrogen, and wherein $R_1$ is as defined above;
(s) removing the C-24 hydroxy protecting group of the compound of general structure Va;
(t) isomerising the compound of general structure Va to the compound of general structure VIa,
wherein X, $R_1$ and $R_2$ are as defined above; and
(u) when $R_1$ is not hydrogen, removing the hydroxy protecting group $R_1$ of the compound of general structure VIa to generate calcipotriol or calcipotriol monohydrate.

In a still further aspect, this invention relates to a method for producing a compound of general structure III,
wherein X represents either hydrogen or $OR_2$,
and wherein $R_1$ and $R_2$ may be the same or different and represent hydrogen, or a hydroxy protecting group,
by reacting a compound of general structure VII or VIII,

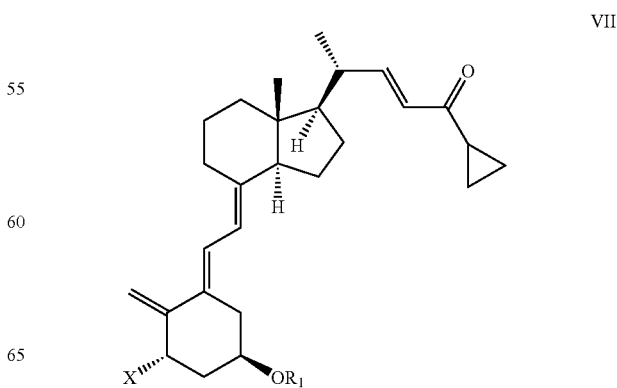

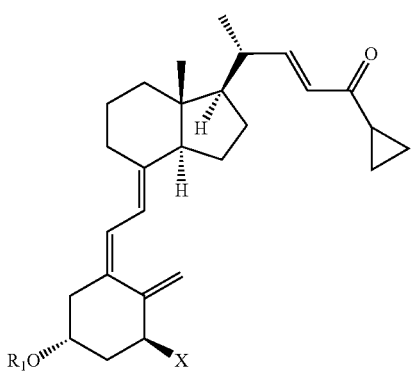

VIII

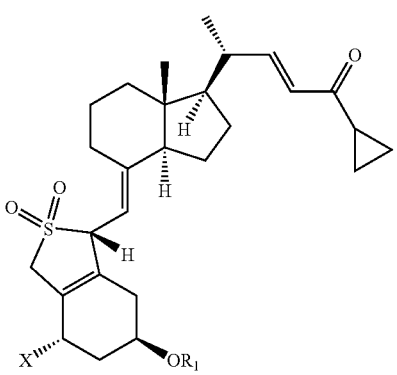

IIIb wherein X represents either hydrogen or OR$_2$,
and wherein R$_1$ and R$_2$ may be the same or different and represent hydrogen, or a hydroxy protecting group.

wherein R$_1$ and R$_2$ are as defined above, with sulphur dioxide.

In a still further aspect, this invention relates to a method of reacting the mixture of compounds of general structure IVa and IVb, wherein X represents either hydrogen or OR$_2$, and wherein R$_1$ and R$_2$ may be the same or different and represent hydrogen, or a hydroxy protecting group, which is enriched with IVa, in the presence of a base to give a mixture of compounds of general structure Va and Vb, which is enriched with Va, wherein X, R$_1$, and R$_2$ are as defined above.

In a still further aspect, this invention relates to a method for producing calcipotriol {(5Z,7E,22E,24S)-24-cyclopropyl-9,10-secochola-5,7,10(19),22-tetraene-1α-3β-24-triol} or calcipotriol monohydrate comprising any one of the methods above.

In a still further aspect, this invention relates to a compound of general structure IIIa or IIIb, or mixtures thereof, In a still further aspect, this invention relates to a compound of general structure IVaa, IVab, IVba, IVbb, IVb, or mixtures thereof,

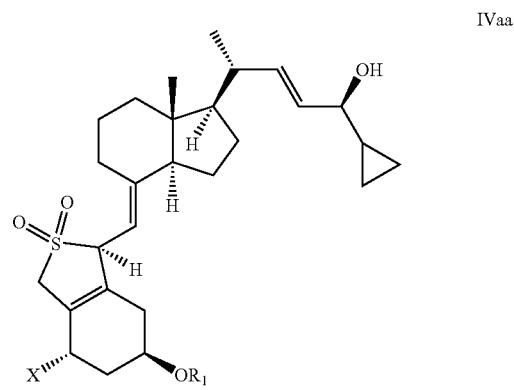

IVaa

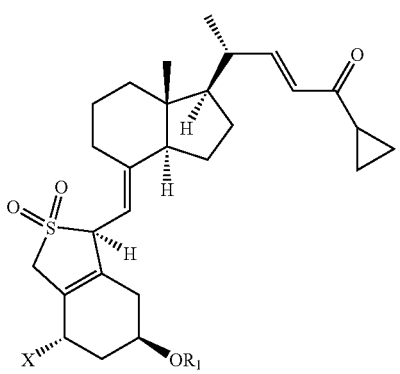

IIIa

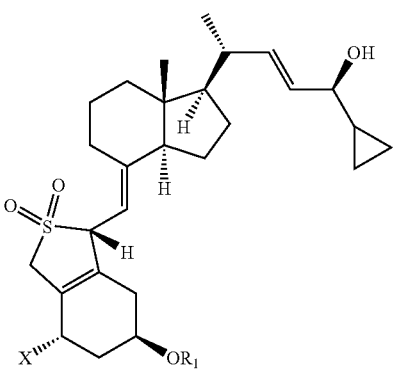

IVab

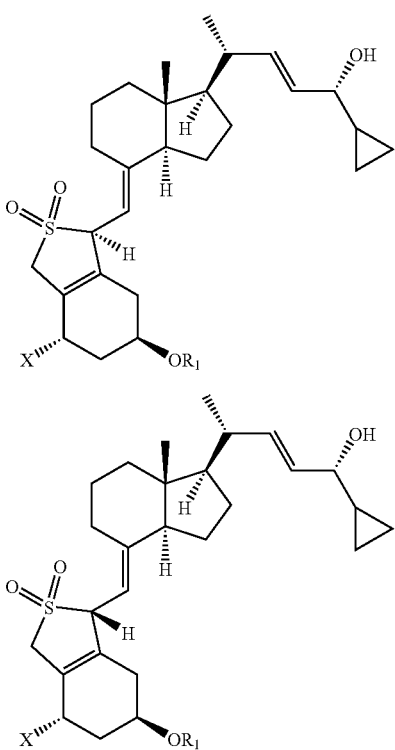

wherein X represents either hydrogen or $OR_2$,
and wherein $R_1$ and $R_2$ may be the same or different and represent hydrogen, or a hydroxy protecting group.

In a still further aspect, this invention relates to the use of a compound of general structure IIIa, IIb, IVaa, IVba, IVab, IVbb as an intermediate in the manufacture of calcipotriol or calcipotriol monohydrate.

DETAILED DESCRIPTION OF THE INVENTION

Definitions

As used herein a "hydroxy protecting group" is any group which forms a derivative that is stable to the projected reactions wherein said hydroxy protecting group can be selectively removed by reagents that do not attack the regenerated hydroxy group. Said derivative can be obtained by selective reaction of a hydroxy protecting agent with a hydroxy group. Silyl derivatives, such as tert-butyldimethylsilyl forming silyl ethers are examples of hydroxy protecting groups. Silyl chlorides such as tert-butyldimethylsilyl chloride (TBSCl), trimethylsilylchloride, triethylsilylchloride, diphenylmethylsilylchloride, triisopropylsilylchloride, and tert-butyldiphenylsilylchloride are examples of hydroxy protecting agents. Hydrogen fluoride, such as aqueous HF in acetonitrile, or tetra n-butylammonium fluoride are examples of reagents which can remove silyl groups. Other hydroxy protecting groups include ethers, such as tetrahydropyranyl (THP) ether, including alkoxyalkyl ethers (acetals), such as methoxymethyl (MOM) ether, or esters, such as chloroacetate ester, trimethylacetate, acetate or benzoate ester. Non-limiting examples of hydroxy protecting groups and methods of protection and removal, all included in the scope of this application, can for example be found in "Protective Groups in Organic Synthesis", $3^{rd}$ ed., T. W. Greene & P. G. M. Wuts eds., John Wiley 1999 and in "Protecting Groups", $1^{st}$ ed., P. J. Kocienski, G. Thieme 2000.

As used herein, "alkyl" is intented to mean a linear or branched alkyl group, which may be cyclic or acyclic, having one to twenty carbon atoms, preferably one to seven carbon atoms. The methyl group, ethyl group, n-propyl group, iso-propyl group, pentyl group, hexyl group, and the tert-butyldimethyl group are non-limiting examples of alkyl groups.

As used herein "reducing agent" is intended to mean any agent capable of reducing, including enantioselectively or diastereoselectively reducing, the C-24 keto group of a compound of general structure III to give a compound of general structure IV. In one embodiment, the reducing agent may reduce the C-24 keto group of a compound of general structure III without a chiral auxiliary to yield a mixture of compounds of general structure IV, wherein said mixture is enriched for the desired epimer IVa (preferably yielding the 24-S isomer). In another embodiment, the reducing agent may reduce the C-24 keto group of a compound of general structure III in the presence of a chiral auxiliary to yield a mixture of compounds of general structure IV, wherein said mixture is enriched for the desired epimer IVa (preferably yielding the 24-S isomer) The reducing agent may be chiral or non-chiral. Examples of reducing agents include, but are not limited to borane reducing agents, metallic hydrides, such as lithium aluminium hydride, sodium borohydride, or $AlH_3$, optionally in the presence of lanthanide salts (e.g. $LaCl_3$, $CeBr_3$, $CeCl_3$), or $NaBH_3(OAc)$, $Zn(BH_4)_2$, and $Et_3SiH$. Other reducing agents include, but are not limited to, hydrogen in the presence of a catalyst, such as platinum or ruthenium, sodium in ethanol, isopropyl alcohol and aluminium isopropoxide, and zinc powder in water or alcohol.

As used herein "borane reducing agent" includes borane or any borane derivative, such as borane complexes with amines or ethers. Non-limiting examples of borane reducing agents e.g. include N,N-diethylaniline-borane, borane-tetrahydrofuran, 9-borabicyclononane (9-BBN), or borane dimethylsulfide.

As used herein, "chiral auxiliary" means any chiral compound or optically active catalyst, e.g. a compound comprising asymmetrically substituted carbon atoms or axially chiral compounds, or mixtures of chiral compounds and/or optically active catalysts, which will improve the yield of a compound of general structure IVa with respect to its epimer (increase the molar ratio IVa:IVb) in the reduction of a compound of general formula III with said reducing agent. Said chiral auxiliaries will thus be any compound which is capable of increasing the stereoselectivity, in the reduction reaction of a compound of general structure III in comparison to the yield or stereoselectivity for IVa without the chiral auxiliary present or involved. Non-limiting examples of chiral auxiliaries include chiral 1,2-amino-alcohols, such as chiral cis-1-amino-2-indanol derivatives, such as (1S,2R)-(−)-cis-1-amino-2-indanol, or cis-1-amino-1,2,3,4-tetrahydronaphthalen-2-ol, such as (1S,2R)-cis-1-amino-1,2, 3,4-tetrahydronaphthalen-2-ol. Other examples are binaphthyl derivatives, such as (R)-2,2'-bis(diphenylphosphino)-1,1'-binaphthyl-ruthenium acetate 2,2'-dihydroxy-1, 1'binaphthyl derivatives. Further examples include but are not limited to (R)-(+)-α,α-diphenyl-2-pyrrolidinmethanol, (R)-(+)-2-amino-4-methyl-1,1-diphenyl-1-pentanol, (R)-(−)-2-amino-3-methyl-1,1-diphenyl-1-butanol, (R)-(+)-2-amino-1,1,3-triphenyl-1-propanol, and (1R,2S)-(−)-2-amino-1,2-diphenyl ethanol.

As used herein, "inert solvent" means any organic solvent compatible with said reducing agent under the reaction conditions employed, or mixtures of such solvents. The choice of such solvent will depend on the specific reducing agent used. Non-limiting examples of inert solvents include hydrocarbons, such as toluene, and ethers, such as tert-butyl methyl ether or tetrahydrofuran.

A mixture of compounds of general structure IVa and IVb, which is enriched with IVa, means a mixture, optionally comprising other compounds or solvents, were the molar ratio (diastereomer ratio) of IVa/IVb is one (50:50) or larger than one, thus that the mixture contains at least 50% of the compound of general structure IVa (containing 50% or less of the compound of general structure IVb).

A mixture of compounds of general structure Va and Vb, which is enriched with Va, means a mixture, optionally comprising other compounds or solvents, were the molar ratio (diastereomer ratio) of Va/Vb is one (50:50) or larger than one, thus that the mixture contains at least 50% of the compound of general structure Va (containing 50% or less of the compound of general structure Vb).

A mixture of compounds of general structure VIa and VIb, which is enriched with VIa, means a mixture, optionally comprising other compounds or solvents, were the molar ratio (diastereomer ratio) of VIa/VIb is one (50:50) or larger than one, thus that the mixture contains at least 50% of the compound of general structure VIa (containing 50% or less of the compound of general structure VIb).

As used herein, "separating a compound" includes the purification and/or isolation of a compound, e.g. to at least 90% purity, such as to at least 95% purity, such as 97% purity, 98% purity, or 99% purity. The term "separating a compound" also includes the meaning of enhancing the concentration of the compound in a mixture of such compounds, optionally comprising solvents, such that the mixture is further enriched with a desired or preferred compound or isomer, such as an epimer, after said separation.

Embodiments

In a currently most preferred embodiment of the present invention X represents $OR_2$.

In a currently preferred embodiment of the present invention $R_1$ and/or $R_2$ represent alkylsilyl, such as tert-butyldimethylsilyl, most preferably $R_1$ and $R_2$ are the same.

In another embodiment of the present invention $R_1$ and $R_2$ represent hydrogen.

In a currently preferred embodiment of the present invention the reducing agent is a borane reducing agent, such as N,N-diethylaniline-borane, borane-tetrahydrofuran, or borane dimethylsulfide.

In a currently preferred embodiment of the invention, the reducing step is carried out with a chiral reducing agent or in the presence of a chiral auxiliary.

In a currently preferred embodiment of the present invention the chiral auxiliary is a chiral 1,2-amino-alcohol, such as a chiral cis-1-amino-2-indanol derivative, such as (1S,2R)-(−)-cis-1-amino-2-indanol.

In a currently preferred embodiment of the present invention the reducing step is carried out at a temperature between 10-20° C., in particular 15-20° C.

In another embodiment of the present invention the molar ratio (diastereomer ratio IVa/IVb) of a mixture of compounds of general structure IVa and IVb, which is enriched with IVa, is larger than 55:45, such as 56:44, such as 57:43, such as 59:41, such as 60:40, such as 63:37, such as 65:35, such as 68:32, such as 70:30, such as 72:28, such as 73:27, such as 74:26, such as 75:25, such as 76:24, such as 77:23, such as 78:22, such as 79:21, such as 80:20.

In another embodiment of the present invention the molar ratio (diastereomer ratio Va/Vb) of a mixture of compounds of general structure Va and Vb, which is enriched with Va, is larger than 55:45, such as 56:44, such as 57:43, such as 59:41, such as 60:40, such as 63:37, such as 65:35, such as 68:32, such as 70:30, such as 72:28, such as 73:27, such as 74:26, such as 75:25, such as 76:24, such as 77:23, such as 78:22, such as 79:21, such as 80:20.

In another embodiment of the present invention the molar ratio (diastereomer ratio VIa/VIb) of a mixture of compounds of general structure VIa and VIb, which is enriched with VIa, is larger than 55:45, such as 56:44, such as 57:43, such as 59:41, such as 60:40, such as 63:37, such as 65:35, such as 68:32, such as 70:30, such as 72:28, such as 73:27, such as 74:26, such as 75:25, such as 76:24, such as 77:23, such as 78:22, such as 79:21, such as 80:20.

In one embodiment of the present invention, the compound of general structure Va is separated, e.g. by chromatography, from the mixture of compounds of general structure Va and Vb which is enriched with Va, wherein X, $R_1$ and $R_2$ are as defined above in (step (c)).

In another embodiment of the present invention, the compound of general structure VIa is separated, by chromatography, from the mixture of compounds of general structure VIa and VIb which is enriched with VIa, wherein X, $R_1$ and $R_2$ are as defined above in (step (g)).

Synthetic Methods

The compounds of general structure III can for example be synthesized via Diels-Alder reaction by treatment of a compound of general structure VII or VIII with sulphur dioxide. The sulphur dioxide used can be liquid, gaseous or being dissolved in a suitable solvent. Suitable solvents for the Diels-Alder reaction are all solvents, which are compatible with the reaction conditions, such as alkanes, such as hexane or heptane, hydrocarbons, such as xylenes, toluene, ethers, such as diethyl ether or methyl-tert-butyl ether (MTBE), acetates, such as ethyl acetate or 2-propyl acetate, halogenated solvents such as dichloromethane, or mixtures of said solvents. In a preferred embodiment the solvent is toluene. In another preferred embodiment the solvent is a mixture of a water immiscible solvent and water, such as toluene and water. The reaction can also be carried out in neat sulphur dioxide without a solvent. A suitable reaction temperature of the process is −50° C. to 60° C., such as −30° C. to 50° C., such as −15° C. to 40° C., such as −5° C. to 30° C., such as 0° C. to 35° C., such as 5° C. to 30° C. most such as 10° C. to 25° C., such as 15° C. to 20° C. In one embodiment the sulphur dioxide is used in excess (mol/mol), such as 5-100 molar excess, such as 7-30 molar excess, such as 10-15 molar excess. Any excess of unreacted sulphur dioxide may be removed from the reaction mixture by e.g. washing with aqueous base, such as aqueous sodium hydroxide or by distilling the sulphur dioxide off, optionally together with a solvent, optionally under reduced pressure. The compounds of general structure III are usually obtained as a mixture of their epimers IIIa and IIIb.

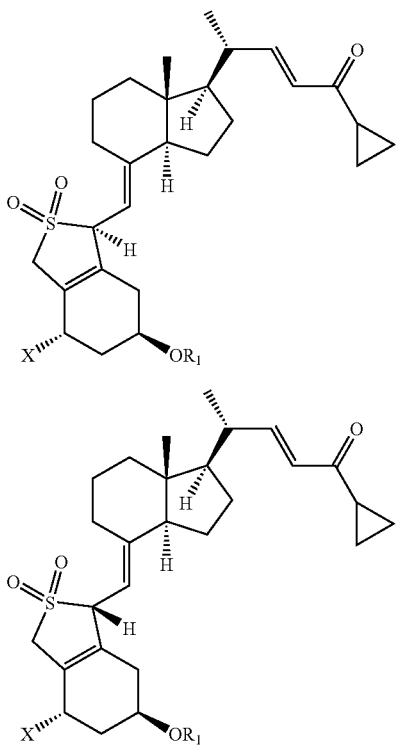

The molar ratio IIIa/IIIb of the mixture of the epimers obtained in the Diels-Alder reaction will depend on the groups X, $R_1$ and $R_2$ and the reaction conditions used. The present invention includes mixtures of all possible compositions (molar ratio IIIa/IIIb), such as 1:99, such as 2:98, such as 3:97, such as 4:96, such as 5:95, such as 10:90, such as 85:15, such as 80:20, such as 75:25, such as 30:70, such as 35:65, such as 40:60, such as 45:55, such as 50:50, such as 55:45, such as 60:40, such as 65:35, such as 70:30, such as 75:25, such as 80:20, such as 85:10, such as 90:10, such as 95:5, such as 96:4, such as 97:3, such as 98:2, such as 99:1.

The general formula III includes mixtures of all possible compositions (molar ratio IIIa/IIIb) as above. In an embodiment of the present invention, compounds IIIa and IIIb are used as a mixture, as indicated in the general formula III in the following reduction step. The mixture of IIIa and IIIb may optionally be purified or separated, such as by chromatography or crystallisation. In another embodiment compound IIIa is used in the following reduction step. In yet another embodiment compound IIIb is used in the following reduction step.

Compounds of general structure VII can for example be synthesised according to methods disclosed for example by M. J. Calverley, Tetrahedron, Vol. 43, No. 20, pp. 4609-4619, 1987 or in WO 87/00834 and references cited therein. For example, compound VII, wherein X is $OR_2$ and both $R_1$ and $R_2$ are tert-butyldimethylsilyl which is described in these references can be deprotected with aqueous hydrofluoric acid in acetonitrile to give a mixture of compounds wherein X is $OR_2$ and either $R_1$ or $R_2$ are hydrogen, or to give a compound wherein X is $OR_2$ and $R_1$ and $R_2$ are both hydrogen. This mixture of compounds can for example be separated by chromatography or crystallisation as generally described herein. By reaction of said compounds of general structure VII, wherein $R_1$ and/or $R_2$ are hydrogen with a suitable protecting agent, new groups $R_1$ and/or $R_2$ can be introduced. Depending on the stoichiometry of the protecting agent used and the reaction conditions, mixtures of unprotected, monoprotected, and diprotected compounds can be obtained. Any intermediate of a mixture wherein X is $OR_2$ and one of $R_1$ or $R_2$ is hydrogen can then be isolated by chromatography and reacted with suitable protecting agent different from the first one used, to give compounds of general structure VII, wherein X is $OR_2$ and $R_1$ is different from $R_2$. Compounds of general structure VII wherein X is hydrogen and $R_1$ is hydrogen or a hydroxy protecting group can for example be prepared starting from compound 7a and/or 7b described by M. J. Calverley, Tetrahedron, Vol. 43, No. 20, p. 4610, 1987 and following analogues procedures and general synthetic methods as above and as described in the above cited references.

The reducing process of the present invention can for example be carried out by reacting a prochiral ketone of general structure III with a chiral borane reducing agent or a borane reducing agent in the presence of a chiral auxiliary. The process results in the enantioselective/diastereoselective reduction of the prochiral ketone, such that one of the two possible epimers IVa or IVb is formed in preference to the corresponding epimer. The degree of enantioselectivity/diastereoselectivity will depend on the reducing agent used, the chiral auxiliary and the reaction conditions.

The reduction reaction of a compound of general structure III is usually carried out in a temperature interval between $-80°$ C. to $70°$ C., such as $-40°$ C. to $60°$ C., such as $-15°$ C. to $50°$ C., such as $-5°$ C. to $40°$ C., e.g. $0°$ C. to $5°$ C. or $5°$ C. to $35°$ C. In one embodiment the temperature interval is between $10°$ C. to $30°$ C., such as $15°$ C. to $25°$ C., such as $15°$ C. to $20°$ C. The optimum temperature will depend on the specific reaction condition and reagents used. In one embodiment of the present invention, the reaction mixture is immediately cooled to $0$-$10°$ C. after completion to avoid the formation of by-products. If N,N-diethylaniline is used as reducing agent, the N,N-diethylaniline formed can be easily removed from the reaction mixture by extraction with aqueous hydrochloric acid. One molar equivalent with respect to the base to be extracted of 1M hydrochloric acid is preferred.

The reducing agent, optionally dissolved or mixed with an inert solvent, may be added to the compound of general structure III optionally dissolved or mixed with an inert solvent, e.g. under an inert atmosphere, such as nitrogen. Alternatively the compound of general structure III, optionally dissolved or mixed with an inert solvent, may be added to the reducing agent, optionally dissolved or mixed with an inert solvent (reversed order).

In one embodiment of the present invention, the reducing agent is used in an equimolar amount or in molar excess to a compound of general structure III. In a specific embodiment of the present invention, the molar ratio of reducing agent/compound of general structure III is 1.0-5.0. In a presently preferred embodiment, the molar ratio of reducing agent/compound of general structure III is 1.8-3.0, such as 2.3-2.9, such as 2.5-2.7.

The chiral auxiliary may react with the reducing agent prior to the reduction in situ to form a chiral reducing agent or the chiral auxiliary may for example serve as a chiral ligand in a complex with the reducing agent, i.e. for example to give a chiral reducing agent. The present invention includes the use of such chiral reducing agents or chiral ligand-reducing agent complexes, which were prepared and isolated separately before being used for the reduction of a compound of general structure III.

The term "reducing agent in the presence of a chiral auxiliary" thus includes any chiral reducing agent. For example, the chiral auxiliary may react with a borane reducing agent prior to the reduction in situ to form a chiral borane reducing agent or the chiral auxiliary may serve as a chiral ligand in a borane complex. Examples of such chiral borane reducing agents are chiral oxaborolidines or oxazaborolidines, such as chiral oxazaborolidine reagents derived from (1R,2S)-cis-1-amino-2-indanol, (1S,2R)-cis-1-amino-2-indanol, (S)-prolinol, (R)-prolinol or B-(3-pinanyl)-9-borabicyclo[3.3.2]nonane(alpine-borane), or e.g. 5,5-diphenyl-2-methyl-3,4-propano-1,3,2-oxazaborolidine, (S)-2-methyl-CBS-oxazaborolidine, (R)-2-methyl-CBS-oxazaborolidine. The present invention therefore includes the use of such chiral reducing agents, such as chiral borane reducing agents, or chiral ligand-reducing agent complexes, such as chiral ligand-borane complexes, which were prepared and isolated before being used for the reduction of a compound of general structure III.

Another example of a chiral ligand in a complex with the reducing agent is the complex of $LiAlH_4$ and 2,2'-dihydroxy-1,1'binaphthyl.

The molar ratio of reducing agent/chiral auxiliary is typically in the range of 0.1-20.0, such as 0.4-10.0, such as 0.3-5.0, such as 0.5-4.5, such as 1.0-4.0, such as 1.9-3.1, such as 2.1-2.9, such as 2.3-2.7, e.g. 10.8, 5.4, 2.6, 2.5, or 1.6.

The chiral auxiliary may be present in catalytic amounts, such as substoichiometric, or equimolar or in molar excess referring to a compound of general structure III or to the reducing agent. E.g. the ratio of chiral auxiliary/compound III may be 0.25-2.5, such as 0.5-2.0, such as 0.8-1.3, such as 0.9-1.2, such as 1.0-1.1.

The selection of a particular enantiomer of the chiral auxiliary will determine the stereoselective orientation of the hydroxy group of the compound of general structure IV with respect to C-24. Chiral auxiliaries which predominantly yield the S-configuration at C-24 are preferred.

Borane-catalysed reactions were for example reviewed by Deloux and Srebnik [Chem. Rev. 93, 763, 1993]. Examples of efficient catalysts based on chiral modified borane can for example be found in [A. Hirao, J. Chem. Soc. Chem. Commun. 315, 1981; E. J. Corey, J. Am. Chem. Soc. 109, 7925, 1987].

Examples of the synthesis and/or use of e.g. 1,2- and 1,3-amino alcohols in stereoselective reduction with borane can e.g. be found in [E. Didier et al.; Tetrahedron 47, 4941-4958, 1991; C. H. Senanayake et al., Tetrahedron Letters, 36(42), 7615-18, 1995, EP 0698028, EP 0640089, EP 0305180, WO 93/23408, WO 94/26751]. The synthesis and/or use of chiral cis-1-amino-2-indanol derivatives in borane reductions can e.g. be found in [C. H. Senanayake, Aldrichimica Acta, 31 (1), 1-15, 1998; A. K. Ghosh et. al., Synthesis, 937-961, 1998; Y. Hong et. al., Tetrahedron Letters, 35(36), 6631-34, 1994; B. Di Simone, Tetrahedron Asymmetry, 6(1) 301-06, 1995; Y. Hong et al., Tetrahedron Letters, 36(36), 6631-34, 1994; R. Hett et al., Org. Process Res. & Dev., 2, 96-99, 1998; or EP 0763005], and references cited therein.

The methods for producing calcipotriol as described herein may be modified with regard to the order of the reaction steps, by omitting one or more reaction steps, or by introducing additional purification or reaction steps at any stage of the reaction sequence. The present invention includes all such modifications.

The method for producing calcipotriol as described herein includes further all variants, where the hydroxy protecting groups $R_1$ and/or $R_2$ for compounds or intermediates, where $R_1$ and/or $R_2$ are not hydrogen, are removed at any stage of the reaction sequence. Compounds or intermediates, wherein $R_1$ and/or $R_2$ are hydrogen may be protected with protecting agents at any stage of the reaction sequence, including protecting agents which yield different protecting groups than those removed earlier in the reaction sequence.

Compounds and intermediates of the present invention may comprise asymmetrically substituted (chiral) carbon atoms and carbon-carbon double bonds which may give rise to the existence of isomeric forms, e.g. enantiomers, diastereomers and geometric isomers.

Epimers are known as diastereomers that have opposite configuration (R or S) at only one of multiple tetrahedral stereogenic centres in molecules having multiple stereogenic centres, such as the vitamin D analogues to which the present invention is directed.

Designation of, for example, C-24 as the epimeric centre of a pair of enantiomers therefore implies that the configuration at the other stereogenic centres of the pair are identical.

The present invention relates to all isomeric forms, such as epimers, either in pure form or as mixtures thereof.

The indication of a specific conformation or configuration either in the formulas or the names of compounds or intermediates of the present invention shall indicate that this specific conformation or configuration is a preferred embodiment of the invention. The indication of a specific conformation or configuration either in the formulas or the names of compounds or intermediates of the present invention shall include any other isomer than specifically indicated, either in pure form or as mixtures thereof, as another embodiment of the present invention.

The indication of an unspecific conformation or configuration either in the formulas or the names of compounds or intermediates of the present invention shall indicate that a mixture of these specific conformations or configurations is a preferred embodiment of the invention. For example, the compound of general formula III is a mixture of the epimers of general formula IIIa and IIIb.

The indication of an unspecific conformation or configuration either in the formulas or the names or numbering of compounds or intermediates of the present invention shall include any specific isomer although not specifically indicated in pure form, e.g. as another embodiment of the present invention.

For example, the compound of general formula IVa includes the following two epimers IVaa and IVab.

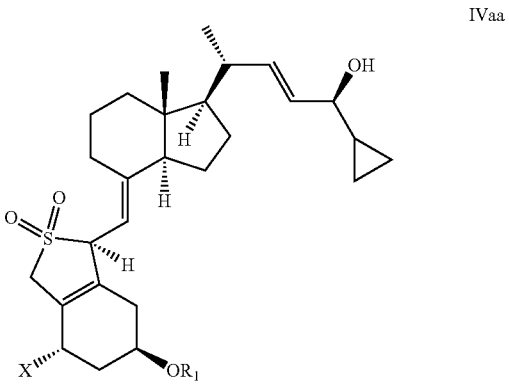

IVaa

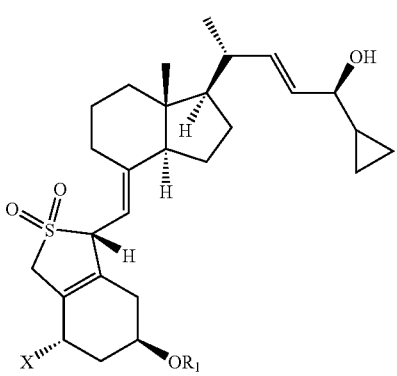

IVab

The meaning of compound of general formula III thus includes epimers IIIa and IIIb.

Pure stereoisomeric forms of the compounds and the intermediates of this invention may be obtained by the application of procedures known in the art, such as by chromatography or crystallisation, or by stereoselective synthesis.

The separation, isolation, and purification methods of the present invention include, but are not limited to chromatography, such as adsorption chromatography (including column chromatography and simulated moving bed (SMB)), crystallisation, or distillation. The separation, isolation, and purification methods may be used subsequently and in combination.

Column chromatography, useful for the separation of vitamin D analogues of the present invention is well known to those skilled in the art of pharmaceutical chemistry. The technique employs a column packed with a stationary phase, for example silica, such as pretreated silica onto which sample to be separated is loaded. The sample is then eluted with a suitable eluent. Elution can be isocratic or so-called solvent programmed (gradient), wherein the composition of the eluent is varied regularly (e.g. linearly) or irregularly (e.g. stepwise over time. Pretreated silica gel, well known to a person skilled in the art of chromatography, is a suitable stationary phase. Elution with 5% (v:v) ethyl acetate in hexane or heptane followed by neat ethyl acetate is but one example of an elution program that produces the desired separation. Other suitable eluents will be deduced by the skilled person through routine methods of development, e.g. by using mixtures of heptane and ethylacetate of suitable polarity.

For the chromatography step, any combination of stationary phase (packing) and eluent that is capable of resolving the mixture of C-24 epimers can be used. Such combinations can be readily determined by the skilled person by routine experimentation. An example of a preferred stationary phase is silica, such as treated silica.

The retro Diels-Alder reaction of the mixture of compounds of general structure IVa and IVb, which is enriched with IVa, in the presence of a base to give a mixture of compounds of general structure Va and Vb, which is enriched with Va, wherein X, $R_1$, and $R_2$ are as defined above, may be carried out in all solvents, which are compatible with the reaction conditions, such as alkanes, such as hexane or heptane, hydrocarbons, such as xylenes, toluene, ethers, such as diethyl ether or methyl-tert-butyl ether (MTBE), acetates, such as ethyl acetate or 2-propyl acetate, halogenated solvents such as dichloromethane, water or mixtures of said solvents.

Methods of said retro Diels Alder reaction are well known to a person skilled in the art of vitamin D synthesis (see e.g. M. J. Calverley, Tetrahedron, Vol. 43, No. 20, pp. 4609-4619, 1987 or in WO 87/00834).

Preferred solvents are toluene, tert-butyl methyl ether, water, or mixtures thereof. Suitable bases to be used in the retro Diels-Alder reaction include, but are not limited to $NaHCO_3$, $KHCO_3$, $Na_2CO_3$, or $K_2CO_3$. In one embodiment of the present invention, the base is aqueous $NaHCO_3$ and/or the retro Diels-Alder reaction is run above 60° C., such as above 70° C., such as between 70° C. and 120° C., such as between 74° C. and 79° C., such as between 72° C. and 78° C.

In one embodiment of the present invention, the temperature range of extractions and phase separations after the completion of the retro Diels-Alder reaction during reaction work-up are about 30° C.-40° C.

Compounds of general structure VIII can be obtained by isomerisation of compounds of general structure VII.

Methods for the isomerisation of compounds of general formula Va and/or Vb to VIa and/or VIb, or VII to VIII, are well known to a person skilled in the art of vitamin D synthesis. Reaction conditions can e.g. be found in M. J. Calverley, Tetrahedron, Vol. 43, No. 20, pp. 4609-4619, 1987 or in WO 87/00834 and references cited therein. In a preferred embodiment of the present invention, the isomerisation is a photo isomerisation, e.g. with UV-light in the presence of a triplet sensitizer, e.g. anthracene or 9-acetylanthracene.

Compounds of general formula III, IV, V, VI, or VII, wherein X=hydrogen may be hydroxylated with a suitable hydroxylating agent, for example by a selenite mediated allylic hydroxylation, under the conditions developed by Hesse, e.g. with $SeO_2$ and N-methylmorpholine N-oxide in refluxing methanol and/or dichloromethane) [D. R. Andrews et al., J. Org. Chem., 1986, 51, 1637) or as described in M. J. Calverley, Tetrahedron, Vol. 43, No. 20, pp. 4609-4619, 1987 or in WO 87/00834, to give compounds of general formula III, IV, V, VI, or VII, wherein X=hydroxy (X=$OR_2$ and $R_2$=hydrogen). The hydroxy groups of the starting materials may be protected with suitable protecting groups such as defined above by methods such as described above, for example to avoid undesired oxidation of said hydroxy groups.

Calcipotriol hydrate may be obtained by crystallisation of calcipotriol from aqueous solvents, such as for example by methods described in WO 94/15912.

EXAMPLES

General:

All chemicals, unless otherwise noted were from commercial sources. All melting points are uncorrected. For $^1H$ nuclear magnetic resonance (NMR) spectra (300 MHz) and $^{13}C$ NMR (75.6 MHz) chemical shift values (δ) (in ppm) are quoted, unless otherwise specified; for deuteriochloroform solutions relative to internal tetramethylsilane (δ=0.00) or chloroform (δ=7.26) or deuteriochloroform (δ=76.81 for $^{13}C$ NMR) standard. The value of a multiplet, either defined (doublet (d), triplet (t), quartet (q)) or not (m) at the approximate mid point is given unless a range is quoted. All organic solvents used were of technical grade. Chromatography was performed on silica gel optionally using the flash technique. The TLC plates coated with silica gel were from Merck KGaA. Preferably the silica used for chromatography was from Merck KGaA Germany: LiChroprep® Si60 (15-25 µm). Ethyl acetate, dichloromethane, hexane, n-hexane, heptane or appropriate mixtures of ethyl acetate, dichloromethane, methanol, and petroleum ether (40-60), hexane or heptane were used as eluents unless otherwise noted. All reactions Compounds of General Structure III Example 1

III: X=OR$_2$, R$_1$, R$_2$=tert-butyldimethylsilyl

1(S),3(R)-bis(tert-butyldimethylsilyloxy)-20(R)-(3'-cyclopropyl-3'-oxoprop-1'(E)-enyl)-9,10-secopregna-5(E),7(E),10(19)-triene SO$_2$-adducts 20(R),1(S),3(R)-bis(tert-butyldimethylsilyloxy)-20-(3'-cyclopropyl-3'-oxoprop-1'(E)-enyl)-9,10-secopregna-5(E),7(E),10(19)-triene (prepared according to the method described by M. J. Calverley, Tetrahedron, Vol. 43, No. 20, pp. 4609-4619, 1987) (20.0 g) was dissolved in toluene (210 ml) at 20° C. followed by the addition of water (40 ml) and SO$_2$ (20 ml) with stirring. When the reaction was judged to be complete by HPLC {Column LiChrosorb Si 60 5 μm 250×4 mm from Merck, 2 ml/min flow, detection at 270 nm & mass detection, hexane/ethyl acetate 9:1 (v:v)}, usually after 2-2.5 hours, a mixture of sodium hydroxide (27.7%, 60 ml) and water (80 ml) was added at 10-18° C. until pH 6 of the reaction mixture. The toluene phase was separated and the solvent removed in vacuo without heating (preferably below 30° C.) to give the two epimeric SO$_2$-adducts IIIa and IIIb as a solid mixture predominantly containing IIIa as checked by TLC. The two epimeric SO$_2$-adducts IIIa and IIIb could be separated by chromatography. Crystalline IIIa could be furthermore obtained by tituration of the solid mixture with methanol. $^1$H NMR (CDCl$_3$) IIIa/X=OR$_2$, R$_1$, R$_2$=tert-butyldimethylsilyl=6.73 (dd, 1H), 6.14 (d, 1H), 4.69 (d, 1H), 4.62 (d, 1H), 4.35 (s, 1H), 4.17 (m, 1H), 3.92 (d, 1H), 3.58 (d, 1H), 2.61 (m, 1H), 2.29 (m, 1H), 2.2-1.2 (m, 16H), 1.11 (d, 3H), 1.05 (m, 2H), 0.90 (m, 2H), 0.87 (s, 9H), 0.85 (s, 9H), 0.68 (s, 3H), 0.06 (s, 3H), 0.05 (s, 3H), 0.04 (s, 3H), 0.02 (s, 3H) ppm.

Preparation 1:

VII: X=OR$_2$, R$_1$, R$_2$=hydrogen

1(S),3(R)-dihydroxy-20(R)-(3'-cyclopropyl-3'-oxoprop-1'(E)-enyl)-9,10-secopregna-5(E),7(E),10(19)-triene 20(R),1(S),3(R)-bis(tert-butyldimethylsilyloxy)-20-(3'-cyclopropyl-3'-oxoprop-1'(E)-enyl)-9,10-secopregna-5(E),7(E),10(19)-triene which was obtained according to the method described by M. J. Calverley, Tetrahedron, Vol. 43, No. 20, p. 4614-4619, 1987 was dissolved in acetonitrile. Aqueous hydrofluoric acid (40%) was added and the mixture was stirred at room temperature for ca. 1 hour. The progress of the reaction could be conveniently checked by TLC using ethyl acetate as an eluent. Ethyl acetate was added to the reaction mixture and the mixture was washed with aqueous sodium hydrocarbonate solution. The organic phase was dried with over MgSO$_4$ and concentrated. The crystals (white needles) which formed were filtered off, washed with ethyl acetate, and dried in vacuo to give the title compound VII (X=OR$_2$, R$_1$, R$_2$=hydrogen). $^1$H NMR (CDCl$_3$) VII/X=OR$_2$, R$_1$, R$_2$=hydrogen=6.77 (dd, 1H), 6.57 (d, 1H), 6.15 (d, 1H), 5.88 (dd, 1H), 5.13 (dd, 1H), 4.98 (s, 1H), 4.50 (m, 1H), 4.23 (m, 1H), 2.86 (m, 2H), 2.29 (m, 2H), 2.14-1.20 (m, 16H), 1.14 (d, 3H), 1.08 (m, 2H), 0.89 (m, 2H), 0.61 (s, 3H), ppm.

Example 2

III: X=OR$_2$, R$_1$, R$_2$=hydrogen

1(S),3(R)-dihydroxy-20(R)-(3'-cyclopropyl-3'-oxoprop-1'(E)-enyl)-9,10-secopregna-5(E),7(E),10(19)-triene SO$_2$-adducts Same method as in Example 1, except that the starting material was 1(S),3(R)-dihydroxy-20(R)-(3'-cyclopropyl-3'-oxoprop-1'(E)-enyl)-9,10-secopregna-5(E),7(E),10(19)-triene from preparation 1. $^1$H NMR (CDCl$_3$) III/X=OR$_2$, R$_1$, R$_2$=hydrogen δ=6.80 (dd, 1H), 6.15 (d, 1H), 4.75 (m, 2H), 4.5-3.9 (m, 4H), 3.70 (d, 1H), 2.60 (m, 1H), 2.5-0.8 (m, 25H), 0.68 (s, 3H), ppm; $^{13}$C NMR (CDCl$_3$) III/X=OR$_2$, R1, R2=hydrogen δ=201.0, 152.1, 151.0, 133.7, 129.2, 128.3, 108.8, 67.3, 65.1, 63.6, 56.1, 55.9, 55.5, 46.5, 40.1, 39.9, 33.9, 29.8, 27.4, 23.9, 22.1, 19.5, 18.9, 12.2, 11.2 ppm.

Preparation 2:

VII: X=OR$_2$, R$_1$=hydrogen, R$_2$=tert-butyldimethylsilyl

1(S)-tert-butyldimethylsilyl-3(R)-hydroxy-20(R)-(3'-cyclopropyl-3'-oxoprop-1'(E)-enyl)-9,10-secopregna-5(E),7(E),10(19)-triene.

20(R),1(S),3(R)-bis(tert-butyldimethylsilyloxy)-20-(3'-cyclopropyl-3'-oxoprop-1'(E)-enyl)-9,10-secopregna-5(E),7(E),10(19)-triene was partially deprotected using the same deprotection conditions as used in Preparation 1 giving a mixture of unreacted starting material, two partially deprotected intermediates and the compound of Preparation 1. Purification by chromatography gave the pure title compound.

The $^1$H NMR was found to be in accordance with the structure. $^1$H NMR (CDCl$_3$) VII/X=OR$_2$, R$_1$=hydrogen, R$_2$=tert-butyldimethylsilyl δ=6.75 (dd, 1H), 6.50 (d, 1H), 6.14 (d, 1H), 5.84 (d, 1H), 5.00 (s, 1H), 4.92 (s, 1H), 4.47 (t, 1H), 4.22 (m, 1H), 2.85 (dd, 1H), 2.62 (dd, 1H), 2.43 (dd, 1H), 2.29 (m, 1H), 2.15-1.15 (m, 15H), 1.11 (d, 3H), 1.06 (m, 2H), 0.87 (s, 9H), 0.86 (m, 2H), 0.59 (s, 3H), 0.06 (s, 3H), 0.04 (s, 3H), ppm.

Example 3

III: X=OR$_2$, R$_1$=hydrogen, R$_2$=tert-butyldimethylsilyl

1(S)-tert-butyldimethylsilyl-3(R)-hydroxy-20(R)-(3'-cyclopropyl-3'-oxoprop-1'(E)-enyl)-9,10-secopregna-5(E),7(E),10(19)-triene SO$_2$-adducts.

Same method as in Example 1, except that the starting material was 1(S)-tert-butyldimethylsilyl-3(R)-hydroxy-20(R)-(3'-cyclopropyl-3'-oxoprop-1'(E)-enyl)-9,10-secopregna-5(E),7(E),10(19)-triene from preparation 2. $^{13}$C NMR (CDCl$_3$) III/X=OR$_2$, R$_1$=hydrogen, R$_2$=tert-butyldimethylsilyl δ=200.3, 151.5, 150.4, 132.0, 129.5, 128.0, 108.5, 66.8, 65.5, 63.8, 56.1, 55.9, 55.2, 46.2, 39.8, 33.6, 29.5, 27.2, 25.4, 23.7, 21.8, 19.2, 18.5, 17.7, 11.8, 10.7, −4.7, −5.2 ppm; $^1$H NMR (CDCl$_3$) IIIb/X=OR$_2$, R$_1$=hydrogen, R$_2$=tert-butyldimethylsilyl δ=6.75 (dd, 1H), 6.14 (d, 1H), 4.80 (d, 1H), 4.65 (d, 1H), 4.43 (m, 1H), 4.25 (m, 1H), 3.92 (d, 1H), 3.63 (dd, 1H), 2.60 (d, 1H), 2.5-1.2 (m, 18H), 1.12 (d, 3H), 1.06 (m, 2H), 0.88 (s, 9H), 0.87 (m, 2H), 0.59 (s, 3H), 0.09 (s, 3H), 0.07 (s, 3H), ppm.

Preparation 3:

VII: X=OR$_2$, R$_1$=COCMe$_3$, R$_2$=tert-butyldimethylsilyl

1(S)-tert-butyldimethylsilyl-3(R)-trimethylacetoxy-20(R)-(3'-cyclopropyl-3'-oxoprop-1'(E)-enyl)-9,10-secopregna-5(E),7(E),10(19)-triene 1(S)-tert-butyldimethylsilyl-3(R)-hydroxy-20(R)-(3'-cyclopropyl-3'-oxoprop-1'(E)-enyl)-9,10-secopregna-5(E),7(E),10(19)-triene from Preparation 2 may be reacted with trimethylacetic acid chloride in the presence of triethylamine in dichloromethane. The obtained raw product may be purified by chromatography to give the pure title compound.

Preparation 4:

VII: X=OR$_2$, R$_1$=COCMe$_3$, R$_2$=hydrogen

1(S)-hydroxy-3(R)-trimethylacetoxy-20(R)-(3'-cyclopropyl-3'-oxoprop-1'(E)-enyl)-9,10-secopregna-5(E),7(E),10(19)-triene.

1(S)-tert-butyldimethylsilyl-3(R)-trimethylacetoxy-20(R)-(3'-cyclopropyl-3'-oxoprop-1'(E)-enyl)-9,10-secopregna-5(E),7(E),10(19)-triene may be deprotected using the same deprotection conditions as used in Preparation 1. The obtained raw product may be purified by chromatography to give the pure title compound.

Example 4

III: X=OR$_2$, R$_1$=COCMe$_3$, R$_2$=hydrogen

1(S)-hydroxy-3(R)-trimethylacetoxy-20(R)-(3'-cyclopropyl-3'-oxoprop-1'(E)-enyl)-9,10-secopregna-5(E),7(E),10(19)-triene SO$_2$-adducts.

Same method as in example 1, except that the starting material was 1(S)-hydroxy-3(R)-trimethylacetoxy-20(R)-(3'-cyclopropyl-3'-oxoprop-1'(E)-enyl)-9,10-secopregna-5(E),7(E),10(19)-triene from preparation 4. $^{13}$C NMR (CDCl$_3$) IIIa/X=OR$_2$, R$_1$=COCMe$_3$, R$_2$=hydrogen δ=200.4, 177.6, 151.6, 150.9, 132.8, 129.3, 128.1, 108.8, 66.9, 66.3, 64.6, 55.8, 55.5, 55.3, 46.3, 39.9, 38.5, 36.3, 30.2, 29.6, 27.2, 26.9, 23.7, 21.8, 19.3, 18.6, 11.9, 10.8 ppm.

Example 5

III: X=OR$_2$, R$_1$=COCMe$_3$, R$_2$=tert-butyldimethylsilyl

1(S)-tert-butyldimethylsilyl-3(R)-trimethylacetoxy-20(R)-(3'-cyclopropyl-3'-oxoprop-1'(E)-enyl)-9,10-secopregna-5(E),7(E),10(19)-triene SO$_2$-adducts.

Same method as in Example 1, except that the starting material was 1(S)-tert-butyldimethylsilyl-3(R)-trimethylacetoxy-20(R)-(3'-cyclopropyl-3'-oxoprop-1'(E)-enyl)-9,10-secopregna-5(E),7(E),10(19)-triene e.g. obtainable from Preparation 3.

Preparation 5:

VII: X=OR$_2$, R$_1$=COMe, R$_2$=hydrogen

1(S)-hydroxy-3(R)-acetoxy-20(R)-(3'-cyclopropyl-3'-oxoprop-1'(E)-enyl)-9,10-secopregna-5(E),7(E),10(19)-triene.

1(S),3(R)-dihydroxy-20(R)-(3'-cyclopropyl-3'-oxoprop-1'(E)-enyl)-9,10-secopregna-5(E),7(E),10(19)-triene (VII: X=OR$_2$, R$_1$, R$_2$=hydrogen) from Preparation 1 may be reacted with one equivalent acetylchloride in the presence of triethylamine. The mixture of products may be purified by chromatography on silica to give the pure title compound.

Example 6

III: X=OR$_2$, R$_1$=COMe, R$_2$=hydrogen

1(S)-hydroxy-3(R)-acetoxy-20(R)-(3'-cyclopropyl-3'-oxoprop-1'(E)-enyl)-9,10-secopregna-5(E),7(E),10(19)-triene SO$_2$-adducts.

Same method as in Example 1, except that the starting material was 1(S)-hydroxy-3(R)-acetoxy-20(R)-(3'-cyclopropyl-3'-oxoprop-1'(E)-enyl)-9,10-secopregna-5(E),7(E),10(19)-triene (VII: X=OR$_2$, R$_1$=COMe, R$_2$=hydrogen) from obtainable from Preparation 5. $^{13}$C NMR (CDCl$_3$) IIIa/X=OR$_2$, R$_1$=COMe, R$_2$=hydrogen δ=200.5, 170.3, 151.6, 150.9, 132.8, 129.2, 128.1, 108.3, 66.8, 66.4, 64.6, 55.9, 55.7, 55.3, 46.3, 39.9, 36.4, 30.4, 29.6, 27.2, 23.7, 21.8, 21.0, 19.3, 18.6, 11.9, 10.8.

Example 7

III: X=OR$_2$, R$_1$=COMe, R$_2$=tert-butyldimethylsilyl

1(S)-tert-butyldimethylsilyl-3(R)-acetoxy-20(R)-(3'-cyclopropyl-3'-oxoprop-1'(E)-enyl)-9,10-secopregna-5(E),7(E),10(19)-triene SO$_2$-adducts.

Same method as in Example 1, except that the starting material was 1(S)-tert-butyldimethylsilyl-3(R)-acetoxy-20(R)-(3'-cyclopropyl-3'-oxoprop-1'(E)-enyl)-9,10-secopregna-5(E),7(E),10(19)-triene. $^1$H NMR (CDCl$_3$) IIIa/X=OR$_2$, R$_1$=COMe, R$_2$=tert-butyldimethylsilyl δ=6.75 (dd, 1H), 6.16 (d, 1H), 5.20 (m, 1H), 4.71 (s, 2H), 4.33 (s, 1H), 3.95 (d, 1H), 3.60 (d, 1H), 2.61 (m, 1H), 2.31 (m, 2H), 2.15-1.2 (m, 15H), 2.03 (s, 3H), 1.11 (d, 3H), 1.07 (m, 2H), 0.89 (m, 2H), 0.88 (s, 9H), 0.68 (s, 3H), 0.08 (s, 3H), 0.07 (s, 3H), ppm.

Example 8

III: X=hydrogen, R$_1$=tert-butyldimethylsilyl

3(R)-tert-butyldimethylsilyloxy-20(R)-(3'-cyclopropyl-3'-oxoprop-1'(E)-enyl)-9,10-secopregna-5(E),7(E),10(19)-triene SO$_2$-adducts The starting material VII, X=hydrogen, R$_1$=tert-butyldimethylsilyl (prepared according to the methods described by M. J. Calverley, Tetrahedron, Vol. 43, No. 20, pp. 4609-4619, 1987) (38.5 g) was dissolved in toluene (550 ml) at 20° C. followed by the addition of water (105 ml) and SO$_2$ (53 ml) with stirring. When the reaction was judged to be complete by HPLC {Column LiChrosorb Si 60 5 μm 250×4 mm from Merck, 2 ml/min flow, detection at 270 nm & mass detection, hexane/ethyl acetate 9:1 (v:v)}, usually after 2-2.5 hours, a mixture of sodium hydroxide (27.7%, 150 ml) and water (480 ml) was added at 10-18° C. until pH 6 of the reaction mixture. The toluene phase was separated and the solvent removed in vacuo without heating (preferably below 30° C.) to give two epimeric SO$_2$-adducts IIIa and IIIb (X=hydrogen, R$_1$=tert-butyldimethylsilyl) as a solid mixture predominantly containing IIIa as checked by TLC. The two epimeric SO$_2$-adducts could be separated by chromatography. Crystalline IIIa could be furthermore obtained by tituration of the solid mixture with methanol. $^{13}$C NMR (CDCl$_3$) (III: X=hydrogen, R$_1$=tert-butyldimethylsilyl, mixture of isomers IIIa and IIIb): 200.3, 151.6, 151.4, 149.8, 149.2, 130.5, 130.1, 128.3, 128.1, 126.6, 126.3, 110.5, 110.0, 67.4, 66.7, 66.6, 66.3, 58.0, 57.9, 55.8, 55.6, 55.3, 55.2, 46.3, 45.5, 39.9, 39.7, 34.4, 34.1, 33.9, 31.4, 30.8, 30.5, 29.6, 29.1, 27.3, 27.1, 26.7, 25.6, 25.1, 24.4, 24.1, 23.6, 23.2, 22.4, 21.9, 21.9, 19.4, 19.3, 18.6, 18.4, 17.9, 17.9, 13.9, 12.2, 11.9, 10.8, −5.0.

Compounds of General Structure IV

Example 9

SO$_2$-adduct of 1(S),3(R)-bis(tert-butyl-dimethylsilyloxy)-20(R)-(3'-cyclopropyl-3'(S)-hydroxyprop-1'(E)-enyl)-9,10-secopregna-5(E),7(E),10(19)-triene (IVa: X=OR$_2$, R$_1$, R$_2$=tert-butyldimethylsilyl), and SO$_2$-adduct of 1(S),3(R)-bis(tert-butyl-dimethylsilyloxy)-20(R)-(3'-cyclopropyl-3(R)'-hydroxyprop-1'(E)-enyl)-9,10-secopregna-5(E),7(E),10(19)-triene (IVb: X=OR$_2$, R$_1$, R$_2$=tert-butyldimethylsilyl)

(1S,2R)-(−)-cis-1-amino-2-indanol (5.0 g) was mixed with MTBE (160 ml) under a nitrogen atmosphere at 15-25° C. followed by the addition of N,N-diethylaniline-borane (16.0 ml) at that temperature. The mixture was stirred until no more evolution of hydrogen could be observed. The mixture of SO$_2$-adducts of 1(S),3(R)-bis(tert-butyl-dimethylsilyloxy)-20(R)-(3'-cyclopropyl-3'-oxoprop-1'(E)-enyl)-9,10-secopregna-5(E),7(E),10(19)-triene (III: X=OR$_2$, R$_1$, R$_2$=tert-butyldimethylsilyl) obtained in Example 1 was dissolved in toluene (160 ml) and MTBE (80 ml). This solution was added dropwise to the borane containing mixture at 15-25° C. The mixture was stirred for ca. 30-60 minutes after complete addition and then quenched with saturated aqueous NaHCO$_3$ (110 ml) at 10-15° C. The organic phase was separated and washed with 1 M hydrochloric acid (100 ml) at 0-10° C. followed by washing with saturated aqueous NaHCO$_3$ (100 ml). The organic phase contained the SO$_2$-adducts of 1(S),3(R)-bis(tert-butyl-dimethylsilyloxy)-20(R)-(3'-cyclopropyl-3(S)'-hydroxyprop-1'(E)-enyl)-9,10-secopregna-5(E),7(E),10(19)-triene (IVa: X=OR$_2$, R1, R2=tert-butyldimethylsilyl), and the SO$_2$-adducts of 1(S),3(R)-bis(tert-butyl-dimethylsilyloxy)-20(R)-(3'-cyclopropyl-3(R)'-hydroxyprop-1'(E)-enyl)-9,10-secopregna-5(E),7(E),10(19)-triene (IVb: X=OR$_2$, R$_1$, R$_2$=tert-butyldimethylsilyl) in a molar ratio of 72-78:22-28 (IVa:IVb) as checked by HPLC-analysis of an aliquot after retro-Diels Alder reaction and analysis according to the method described in example 10}. Compound IVaa was isolated by chromatography on silica.
$^{13}$C NMR (CDCl$_3$) IVa/X=OR$_2$, R$_1$, R$_2$=tert-butyldimethylsilyl δ=150.6, 137.6, 132.3, 129.3, 128.8, 109.0, 76.9, 67.3, 65.8, 64.5, 56.2, 56.1, 55.9, 46.0, 40.5, 40.0, 39.6, 34.1, 29.6, 27.4, 25.6, 25.5, 23.8, 21.8, 20.3, 17.8, 17.7, 17.4, 11.8, 2.8, 1.7, −4.7, −5.0, −5.0, −5.2 ppm.

Example 10

SO$_2$-adducts of 3(R)-tert-butyl-dimethylsilyloxy-20 (R)-(3'-cyclopropyl-3'(S)-hydroxyprop-1'(E)-enyl)-9, 10-secopregna-5(E),7(E),10(19)-triene (IVa: X=hydrogen, R$_1$=tert-butyldimethylsilyl), and SO$_2$-adducts of 3(R)-tert-butyl-dimethylsilyloxy-20(R)-(3'-cyclopropyl-3'(R)-hydroxyprop-1'(E)-enyl)-9,10-secopregna-5(E),7(E),10(19)-triene
(IVb: X=hydrogen, R$_1$=tert-butyldimethylsilyl), (1S,2R)-(−)-cis-1-amino-2-indanol (1.22 g, 1.08 eq.) was mixed with MTBE (36 ml) under a nitrogen atmosphere at 15-25° C. followed by the addition of N,N-diethylaniline-borane (3.6 ml, 2.7 eq.) at that temperature. The mixture was stirred until no more evolution of hydrogen could be observed. The mixture of SO$_2$-adducts of 3(R)-tert-butyl-dimethylsilyloxy-20(R)-(3'-cyclopropyl-3'-oxoprop-1'(E)-enyl)-9,10-secopregna-5(E),7(E),10(19)-triene (III: X=hydrogen, R$_1$=tert-butyldimethylsilyl) obtained in Example 8 (4.32 g) was dissolved in a mixture of MTBE (18 ml) and toluene (36 ml) at room temperature and then added dropwise to the borane containing mixture at 15-25° C. over 15 min. The mixture was stirred for ca. 60 minutes after complete addition and then quenched with saturated aqueous NaHCO$_3$ (25 ml). The organic phase was separated and washed with 1 M hydrochloric acid (25 ml) at 0-10° C. followed by washing with saturated aqueous NaHCO$_3$ (25 ml) at 10-20° C. The organic phase contained the SO$_2$-adducts of 3(R)-tert-butyl-dimethylsilyloxy-20(R)-(3'-cyclopropyl-3'(S)-hydroxyprop-1'(E)-enyl)-9,10-secopregna-5 (E),7(E),10(19)-triene (IVa: X=hydrogen, R$_1$=tert-butyldimethylsilyl), and the SO$_2$-adducts of 3(R)-tert-butyldimethylsilyloxy-20(R)-(3'-cyclopropyl-3(R)'-hydroxyprop-1'(E)-enyl)-9,10-secopregna-5(E),7(E),10 (19)-triene (IVb: X=hydrogen, R$_1$=tert-butyldimethylsilyl).

Compounds of General Structure V

Example 11

1(S),3(R)-bis(tert-butyl-dimethylsilyloxy)-20(R)-(3'-cyclopropyl-3(S)'-hydroxyprop-1'(E)-enyl)-9,10-secopregna-5(E),7(E),10(19)-triene (Va: X=OR$_2$, R$_1$, R$_2$=tert-butyldimethylsilyl), and 1(S),3(R)-bis(tert-butyl-dimethylsilyloxy)-20(R)-(3'-cyclopropyl-3(R)'-hydroxyprop-1'(E)-enyl)-9,10-secopregna-5(E),7(E),10(19)-triene
(Vb: X=OR$_2$, R$_1$, R$_2$=tert-butyldimethylsilyl)

The organic phase from Example 9 containing the SO$_2$-adducts of IVa (X=OR$_2$, R$_1$, R$_2$=tert-butyldimethylsilyl), and IVb (X=OR$_2$, R$_1$, R$_2$=tert-butyldimethylsilyl) was stirred vigorously with saturated aqueous NaHCO$_3$ (110 ml) and then heated (bath temperature ca. 90° C.) where the MTBE was distilled off. Conveniently the retro Diels-Alder reaction could be checked by HPLC HPLC {Column LiChrosorb Si 60 250×4 mm from Merck, 1 ml/min flow, detection at 270 nm, hexane/ethyl acetate 9:1.5 (v:v)}. After completion (usually 2-2.5 hours), the reaction mixture was cooled to 30-40° C. and the organic phase was separated, washed with saturated aqueous NaHCO$_3$ (110 ml) and water (100 ml). The solvent was removed in vacuo and the obtained oil (29 g) was dissolved in hexane (200 ml). The organic mixture was cooled to ca. −15° C., filtered over a short path of silica, and the remainder washed with hexane (ca. 100 ml). The hexane phase was washed with a mixture of methanol and water (1:2) and the organic solvent was removed in vacuo. The remaining oil, containing a mixture of 1(S),3(R)-bis(tert-butyl-dimethylsilyloxy)-20(R)-(3'-cyclopropyl-3(S)'-hydroxyprop-1'(E)-enyl)-9,10-secopregna-5(E),7(E),10 (19)-triene (Va: X=OR$_2$, R$_1$, R$_2$=tert-butyldimethylsilyl), and 1(S),3(R)-bis(tert-butyl-dimethylsilyloxy)-20(R)-(3'-cyclopropyl-3(R)'-hydroxyprop-1'(E)-enyl)-9,10-secopregna-5(E),7(E),10(19)-triene (Vb: X=OR$_2$, R$_1$, R$_2$=tert-butyldimethylsilyl) in a molar ratio of a range of 72-78:22-28 (Va:Vb) as checked by HPLC {Column LiChrosorb Si 60 5 μm 250×4 mm from Merck, 1 ml/min flow, detection at 270 nm, n-heptane/2-propanol 100:0.25 (v:v): RT Va ca. 14.3 min, Vb: 11.9 min; or hexane/ethyl acetate 90:15 (v:v): RT Va ca. 7.6 min, Vb: 6.4 min}, was purified by chromatography as described earlier by M. J. Calverley, Tetrahedron, Vol. 43, No. 20, pp. 4609-4619, 1987 or in WO 87/00834, to give 10.9 g (98.9% HPLC purity) of Va/X=OR$_2$, R$_1$, R$_2$=tert-butyldimethylsilyl after crystallisation from a mixture of hexane and methanol and a small amount of triethylamine (by slowly evaporating the hexane followed by cooling to −15° C.), in full accordance with the data described by M. J. Calverley in Tetrahedron, Vol. 43, No. 20, p. 4617, 1987 for compound 22.
$^{13}$C NMR (CDCl$_3$) Va/X=OR$_2$, R$_1$, R$_2$=tert-butyldimethylsilyl δ=153.4, 142.9, 137.9, 135.2, 128.7, 121.5, 116.3, 106.4, 77.1, 70.0, 67.0, 56.2, 55.8, 45.7, 43.7, 40.2, 39.8, 36.3, 28.7, 27.5, 25.6, 25.6, 23.3, 22.0, 20.3, 18.0, 17.9, 17.4, 12.1, 2.9, 1.6, −5.0, −5.0, −5.1; Vb/X=OR$_2$, R$_1$, R$_2$=tert-butyldimethylsilyl, δ=153.5, 142.9, 137.6, 135.3, 128.7, 121.5, 116.3, 106.4, 76.8, 70.0, 67.0, 56.2, 56.0, 45.7, 43.8, 40.2, 39.7, 36.4, 28.7, 27.6, 25.7, 25.6, 23.3, 22.0, 20.3, 18.0, 17.9, 17.3, 12.1, 2.8, 1.6, −5.0, −5.1, −5.1 ppm.

Example 12

3(R)-tert-butyl-dimethylsilyloxy-20(R)-(3'-cyclopropyl-3(S)'-hydroxyprop-1'(E)-enyl)-9,10-secopregna-5(E),7(E),10(19)-triene (Va: X=hydrogen, $R_1$=tert-butyldimethylsilyl), and
3(R)-tert-butyl-dimethylsilyloxy-20(R)-(3'-cyclopropyl-3(R)'-hydroxyprop-1'(E)-enyl)-9,10-secopregna-5(E),7(E),10(19)-triene
(Vb: X=hydrogen, $R_1$=tert-butyldimethylsilyl)

The organic solution from Example 10 containing the $SO_2$-adducts of IVa (X=hydrogen, $R_1$=tert-butyldimethylsilyl), and IVb (X=hydrogen, $R_1$=tert-butyldimethylsilyl) was stirred vigorously with saturated aqueous $NaHCO_3$ (25 ml) and then heated (bath temperature ca. 90° C.) where the MTBE was distilled off. Conveniently the retro Diels-Alder reaction could be checked by HPLC HPLC {Column LiChrosorb Si 60 250×4 mm from Merck, 1 ml/min flow, detection at 270 nm, hexane/ethyl acetate 9:1.5 (v:v)}. After completion (approx. 2 hours), the reaction mixture was cooled to 15-25° C. and the organic phase was separated, washed with water (25 ml)., containing a mixture of Va:Vb (X=hydrogen, $R_1$=tert-butyldimethylsilyl) in a molar ratio of (75:25) as checked by HPLC {Column LiChrosorb Si 60 5 μm 250×4 mm from Merck, 1 ml/min flow, detection at 270 nm, hexane/ethylacetate 90:15 (v:v): RT Vb: ca. 6.1 min, RT Va: ca. 7.4 min}. $^1$H NMR ($CDCl_3$) Va/X=hydrogen, $R_1$=tert-butyldimethylsilyl δ=6.45 (d, 1H), 5.84 (d, 1H), 5.46 (m, 2H), 4.92 (s, 1H), 4.63 (s, 1H), 3.84 (m, 1H), 3.42 (m, 1H), 2.85 (d, 1H), 2.64 (d, 1H), 2.45 (m, 1H), 2.32-1.18 (m, 17H), 1.04 (d, 3H), 0.98 (m, 1H), 0.87 (s, 9H), 0.56 (s, 3H), 0.51 (m, 2H), 0.32 (m, 1H), 0.22 (m, 1H), 0.05 (s, 3H), 0.04 (s, 3H); Vb/X=hydrogen, $R_1$=tert-butyldimethylsilyl δ=6.45 (d, 1H), 5.83 (d, 1H), 5.47 (m, 2H), 4.90 (s, 1H), 4.62 (s, 1H), 3.83 (m, 1H), 3.45 (m, 1H), 2.83 (d, 1H), 2.62 (d, 1H), 2.44 (m, 1H), 2.24 (m, 1H), 2.18-1.17 (m, 16H), 1.03 (d, 3H), 0.96 (m, 1H), 0.86 (s, 9H), 0.55 (s, 3H), 0.50 (m, 2H), 0.30 (m, 1H), 0.20 (m, 1H), 0.05 (s, 3H), 0.04 (s, 3H).

Compounds of General Structure VI

Example 13

1(S),3(R)-bis(tert-butyl-dimethylsilyloxy)-20(R)-(3'-cyclopropyl-3(S)'-hydroxyprop-1'(E)-enyl)-9,10-secopregna-5(Z),7(E),10(19)-triene (X=$OR_2$, VIa: $R_1$, $R_2$=tert-butyldimethylsilyl)
1(S),3(R)-bis(tert-butyl-dimethylsilyloxy)-20(R)-(3'-cyclopropyl-3(S)'-hydroxyprop-1'(E)-enyl)-9,10-secopregna-5(E),7(E),10(19)-triene (Va: X=$OR_2$, $R_1$, $R_2$=tert-butyldimethylsilyl) obtained in Example 11 was photosisomerised in toluene using a high pressure ultraviolet lamp at 20° C. as described earlier by M. J. Calverley, Tetrahedron, Vol. 43, No. 20, pp. 4609-4619, 1987 or in WO 87/00834, except that 9-acetylanthracene was used instead of anthracene, to give 1(S),3(R)-bis(tert-butyl-dimethylsilyloxy)-20(R)-(3'-cyclopropyl-3(S)'-hydroxyprop-1'(E)-enyl)-9,10-secopregna-5(Z),7(E),10(19)-triene (VIa: X=$OR_2$, $R_1$, $R_2$=tert-butyldimethylsilyl) after chromatography in full accordance with the data described by M. J. Calverley in Tetrahedron, Vol. 43, No. 20, p. 4618, 1987 for compound 28.

Calcipotriol

Example 14

1(S),3(R)-dihydroxy-20(R)-(3'-cyclopropyl-3(S)'-hydroxyprop-1'(E)-enyl)-9,10-secopregna-5(Z),7(E), 10(19)-triene 1(S),3(R)-bis(tert-butyl-dimethylsilyloxy)-20(R)-(3'-cyclopropyl-3(S)'-hydroxyprop-1'(E)-enyl)-9,10-secopregna-5(Z),7(E),10(19)-triene (VIa: X=$OR_2$, $R_1$, $R_2$=tert-butyldimethylsilyl) obtained in Example 13 was deprotected using tetrabutyl ammonium fluoride in tetrahydrofuran at 60° C. followed by chromatography, as described earlier by M. J. Calverley, Tetrahedron, Vol. 43, No. 20, pp. 4609-4619, 1987 or in WO 87/00834. Crystallisation from ethylacetate/hexane containing a few drops of triethylamine gave calcipotriol in full accordance with the data described by M. J. Calverley in Tetrahedron, Vol. 43, No. 20, p. 4618, 1987 for compound 4.

Calcipotriol Monohydrate

Example 15

The calcipotriol obtained in Example 14 was crystallised from ethyl acetate/water as described in WO 94/15912 to give calcipotriol monohydrate in full accordance with the characteristic data described in that patent.

Diastereoselective Reduction Under Various Reducing Conditions

Example 16

TABLE 1

Diastereoselective reduction of compounds of general structure III, where X = $OR_2$ and $R_1$ and $R_2$ = tert-butyldimethylsilyl (mixture of 1(S),3(R)-bis(tert-butyldimethylsilyloxy)-20(R)-(3'-cyclopropyl-3'-oxoprop-1'(E)-enyl)-9,10-secopregna-5(E),7(E),10(19)-triene $SO_2$-adducts from Example 1 following a procedure analogous to Example 9 followed by cheletropic extrusion of sulfur dioxide following a procedure analogous to Example 11 to yield compounds of general structure. Va: X = $OR_2$, $R_1$, $R_2$ = tert-butyldimethylsilyl and Vb: X = $OR_2$, $R_1$, $R_2$ = tert-butyldimethylsilyl under various conditions (eq. = molar equivalents relative to III; MTBE = tert-butylmethyl ether; DEANB = N,N-diethylaniline borane).

| Chiral Auxiliary (eq.) | Reducing reagent (eq.) | Temp. (° C.) | Solvent | Ratio Va:Vb (%) |
|---|---|---|---|---|
| (1S,2R)-(−)-cis-1-amino-2-indanol (1.1 eq.) | DEANB (2.7 eq.) | 15-20 | MTBE/toluene | 72:28 |
| (1S,2R)-(−)-cis-1-amino-2-indanol (1.1 eq.) | DEANB (2.7 eq.) | 20-25 | MTBE/toluene | 72:28 |
| (1S,2R)-(−)-cis-1-amino-2-indanol (1.1 eq.) | DEANB (2.7 eq.) | 10-15 | MTBE/toluene | 70:30 |
| (1S,2R)-(−)-cis-1-amino-2-indanol (0.5 eq.) | DEANB (2.7 eq.) | 15-20 | MTBE/toluene | 72:28 |
| (1S,2R)-(−)-cis-1-amino-2-indanol (0.25 eq.) | DEANB (2.7 eq.) | 15-20 | MTBE/toluene | 56:44 |
| (1S,2R)-(−)-cis-1-amino-2-indanol (1.1 eq.) | DEANB (1.8 eq.) | 15-20 | MTBE/toluene | 59:41 |
| (1S,2R)-(−)-cis-1-amino-2-indanol (1.1 eq.) | $BH_3$•THF (2.7 eq.) | 15-20 | MTBE/toluene | 75:25 |
| (1S,2R)-(−)-cis-1-amino-2-indanol (1.1 eq.) | $BH_3$•$SMe_2$ (2.7 eq.) | 15-20 | MTBE/toluene | 73:27 |
| (1S,2R)-(−)-cis-1-amino-2-indanol (1.1 eq.) | DEANB (2.7 eq.) | 15-20 | THF | 63:37 |

TABLE 1-continued

Diastereoselective reduction of compounds of general structure III, where X = OR₂ and R₁ and R₂ = tert-butyldimethylsilyl (mixture of 1(S),3(R)-bis(tert-butyldimethylsilyloxy)-20(R)-(3'-cyclopropyl-3'-oxoprop-1'(E)-enyl)-9,10-secopregna-5(E),7(E),10(19)-triene SO₂-adducts from Example 1 following a procedure analogous to Example 9 followed by cheletropic extrusion of sulfur dioxide following a procedure analogous to Example 11 to yield compounds of general structure. Va: X = OR₂, R₁, R₂ = tert-butyldimethylsilyl and Vb: X = OR₂, R₁, R₂ = tert-butyldimethylsilyl under various conditions (eq. = molar equivalents relative to III; MTBE = tert-butylmethyl ether; DEANB = N,N-diethylaniline borane).

| Chiral Auxiliary (eq.) | Reducing reagent (eq.) | Temp. (°C.) | Solvent | Ratio Va:Vb (%) |
|---|---|---|---|---|
| (R)-(+)-α,α-Diphenyl-2-pyrrolidinmethanol (1 eq.) | DEANB (2.7 eq.) | 15-20 | MTBE/toluene | 68:32 |
| (R)-(+)-2-Amino-4-methyl-1,1-diphenyl-1-pentanol (0.5 eq.) | DEANB (2.7 eq.) | 15-20 | MTBE/toluene | 72:28 |
| (R)-(−)-2-Amino-3-methyl-1,1-diphenyl-1-butanol (0.5 eq.) | DEANB (2.7 eq.) | 15-20 | MTBE/toluene | 76:24 |
| (R)-(+)-2-amino-1,1,3-triphenyl-1-propanol (0.5 eq.) | DEANB (2.7 eq.) | 15-20 | MTBE/toluene | 74:26 |
| (1R,2S)-(−)-2-Amino-1,2-diphenyl ethanol (0.5 eq.) | DEANB (2.7 eq.) | 15-20 | MTBE/toluene | 57:43 |

The invention claimed is:

1. A method of reducing a compound of structure III,

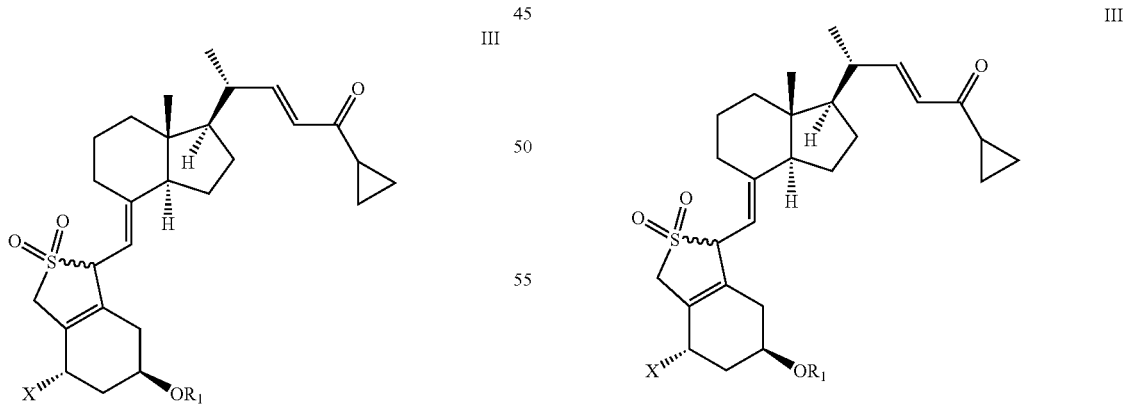

wherein X represents either hydrogen or OR₂,
and wherein R₁ and R₂ may be the same or different and represent hydrogen, or a hydroxy protecting group,
in an inert solvent with a chiral reducing agent or with a reducing agent in the presence of a chiral auxiliary,
to give a mixture of compounds of structure IVa and IVb,

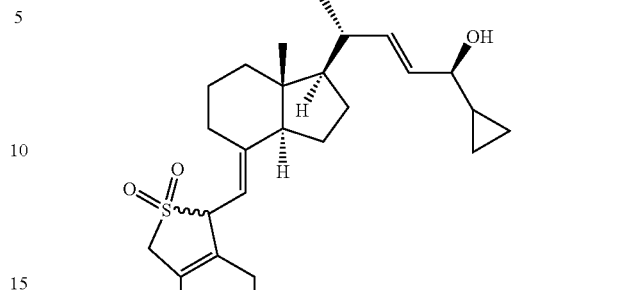

which is enriched with IVa, wherein X, R₁, and R₂ are as defined above.

2. A method for producing calcipotriol {(5Z,7E,22E,24S)-24-cyclopropyl-9,10-secochola-5,7,10(19),22-tetraene-1α-3β-24-triol} or calcipotriol monohydrate comprising the steps of:

(a) reducing a compound of structure III according to claim 1, wherein X represents OR₂,
and wherein R₁ and R₂ may be the same or different and represent hydrogen or a hydroxy protecting group,
in an inert solvent with a chiral reducing agent or with a reducing agent in the presence of a chiral auxiliary,
to give a mixture of compounds of structure IVa and IVb, which is enriched with IVa,

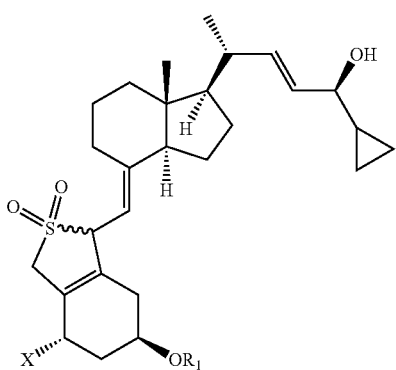

IVa

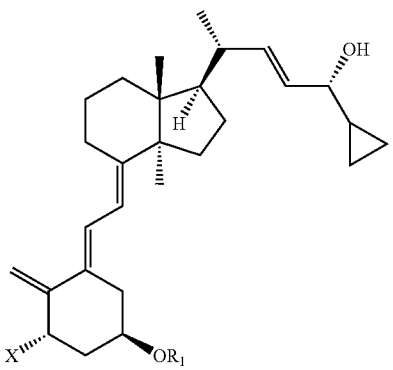

Vb wherein X, R$_1$ and R$_2$ are as defined above;

(c) separating the compound of structure Va from the mixture of compounds of structure Va and Vb which is enriched with Va, wherein X, R$_1$ and R$_2$ are as defined above;

(d) isomerising the compound of structure Va to the compound of structure VIa,

IVb wherein X, R$_1$ and R$_2$ are as defined above;

(b) reacting the mixture of compounds of structure IVa and IVb, which is enriched with IVa, in the presence of a base to give a mixture of compounds of structure Va and Vb, which is enriched with Va,

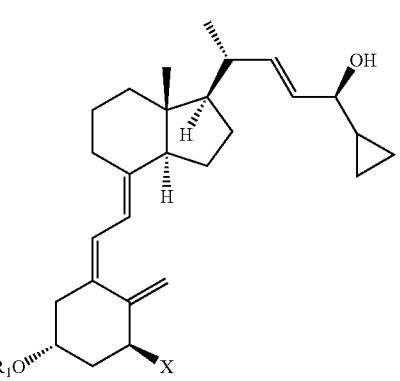

VIa

Va wherein X, R$_1$ and R$_2$ are as defined above; and (e) when R$_1$ and/or R$_2$ are not hydrogen, removing the hydroxy protecting group(s) R$_1$ and/or R$_2$ of the compound of structure VIa to generate calcipotriol or calcipotriol monohydrate.

3. A method for producing calcipotriol or calcipotriol monohydrate comprising steps (a)-(b) of claim 2 and further comprising the steps of:

(f) isomerising the mixture of compounds of structure Va and Vb, wherein X, R$_1$ and R$_2$ are as defined in claim 2, which is enriched with Va, to a mixture of compounds of structure VIa and VIb, which is enriched with VIa, VIa

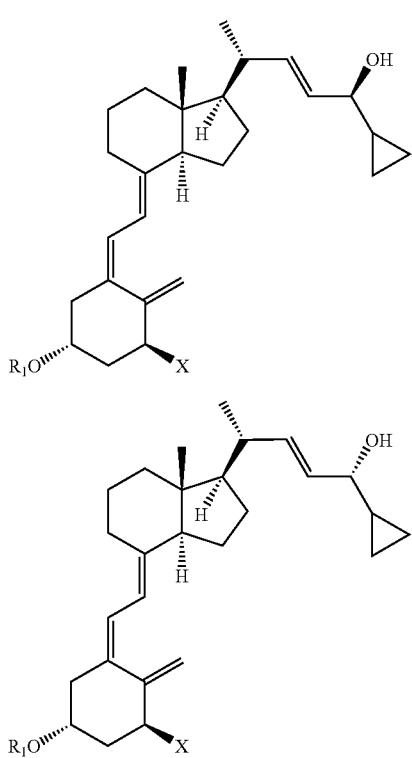

VIb wherein X, R₁ and R₂ are as defined above;

(g) separating the compound of structure VIa from the mixture of compounds of structure VIa and VIb which is enriched with VIa, wherein X, R₁ and R₂ are as defined above;

(h) when R₁ and/or R₂ are not hydrogen, removing the hydroxy protecting group(s) R₁ and/or R₂ of the compound of structure VIa to generate calcipotriol or calcipotriol monohydrate.

4. A method for producing calcipotriol {(5Z,7E,22E,24S)-24-cyclopropyl-9,10-secochola-5,7,10(19),22-tetraene-1α-3β-24-triol} or calcipotriol monohydrate comprising the steps of:

(j) reducing a compound of structure III according to claim 1,

III

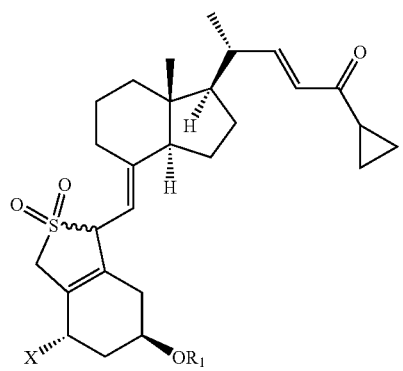

wherein X represents hydrogen, and wherein R₁ represents hydrogen or a hydroxy protecting group, in an inert solvent with a chiral reducing agent or with a reducing agent in the presence of a chiral auxiliary, to give a mixture of compounds of structure IVa and IVb, which is enriched with IVa, IVa

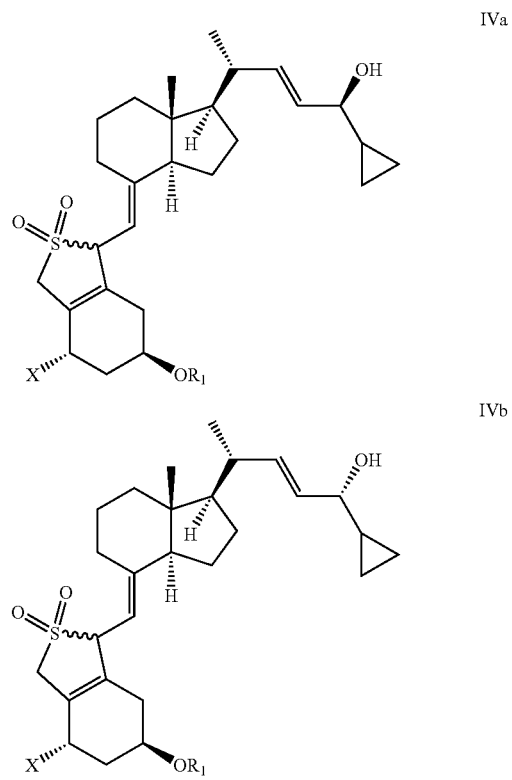

IVb wherein X and R₁ are as defined above;

(k) reacting the mixture of compounds of structure IVa and IVb, which is enriched with IVa, in the presence of a base to give a mixture of compounds of structure Va and Vb, which is enriched with Va, Va

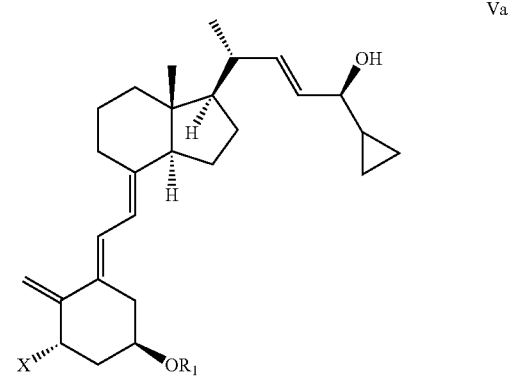

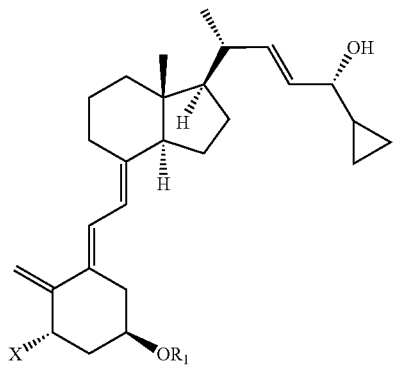

Vb wherein X and R₁ are as defined above;

(l) separating the compound of structure Va from the mixture of compounds of structure Va and Vb which is enriched with Va, wherein X and R₁ are as defined above;

(m) hydroxylating the compound of structure Va with a suitable hydroxylating agent, wherein X and R₁ are as defined above to give a compound of structure Va, wherein X represents $OR_2$ and $R_2$ represents hydrogen, and wherein R₁ is as defined above;

(o) isomerising the compound of structure Va to the compound of structure VIa,

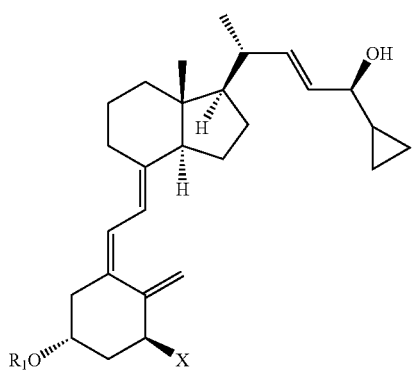

VIa wherein X, R₁ and R₂ are as defined above; and (p) when R₁ is not hydrogen, removing the hydroxy protecting group R₁ of the compound of structure VIa to generate calcipotriol or calcipotriol monohydrate.

5. A method for producing calcipotriol or calcipotriol monohydrate comprising steps (j)-(l) of claim 4 and further comprising the steps of:

(q) protecting the C-24 hydroxy group of the compound of structure Va,

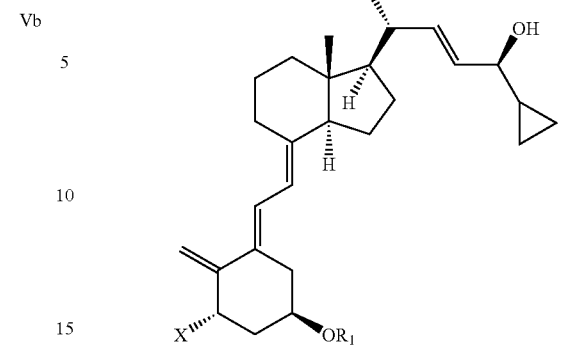

Va wherein X represents hydrogen, and wherein R₁ represents hydrogen or a hydroxy protecting group, with a hydroxy protecting group;

(r) hydroxylating the C-24 hydroxy protected compound of structure Va with a suitable hydroxylating agent, wherein X and R₁ are as defined above to give a C-24 hydroxy protected compound of structure Va, wherein X represents $OR_2$ and $R_2$ represents hydrogen, and wherein R₁ is as defined above;

(s) removing the C-24 hydroxy protecting group of the compound of structure Va;

(t) isomerising the compound of structure Va to the compound of structure VIa,

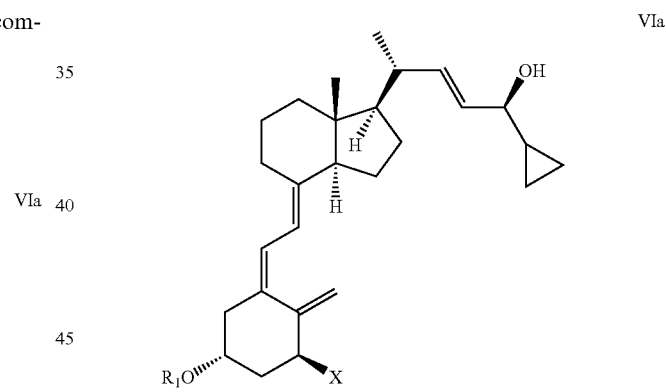

VIa wherein X, R₁ and R₂ are as defined above; and (u) when R₁ is not hydrogen, removing the hydroxy protecting group R₁ of the compound of structure VIa to generate calcipotriol or calcipotriol monohydrate.

6. The method according to claim 1, wherein the reducing agent is a borane derivative.

7. The method according to claim 1, wherein the reducing step is with a reducing agent in the presence of a chiral auxiliary and wherein the reducing agent is N,N-diethylaniline-borane, borane-tetrahydrofuran, or borane dimethylsulfide.

8. The method according to claim 1, wherein the reducing step is with a reducing agent in the presence of a chiral auxiliary and wherein the chiral auxiliary is a chiral 1,2-amino-alcohol.

9. The method according to claim 1, wherein the reducing step is with a reducing agent in the presence of a chiral auxiliary and wherein the chiral auxiliary is a chiral cis-1-amino-2-indanol derivative.

10. The method according to claim 1, wherein the reducing step is with a reducing agent in the presence of a chiral auxiliary and wherein the chiral auxiliary is (1S,2R)-(−)-cis-1-amino-2-indanol.

11. The method according to claim 1, wherein the inert solvent is toluene, tert-butyl methyl ether, tetrahydrofuran, or mixtures thereof.

12. The method according to claim 1, wherein the mixture of compounds of structure IVa and IVb obtained by reducing a compound of structure III has a molar ratio of IVa:IVb which is at least 56:44.

13. The method according to claim 10, wherein the reducing step is carried out at a temperature between 10-20° C.

14. A method of reacting the mixture of compounds of structure IVa and IVb,

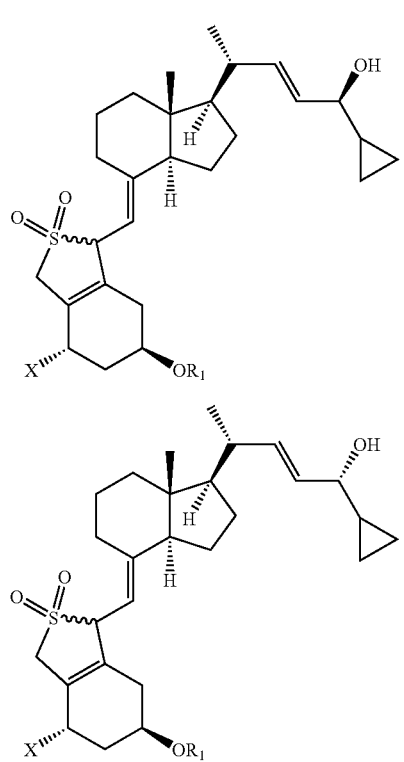

wherein X represents either hydrogen or $OR_2$,
and wherein $R_1$ and $R_2$ may be the same or different and represent hydrogen, or a hydroxy protecting group,
which is enriched with IVa, in the presence of a base to give a mixture of compounds of structure Va and Vb, which is enriched with Va,

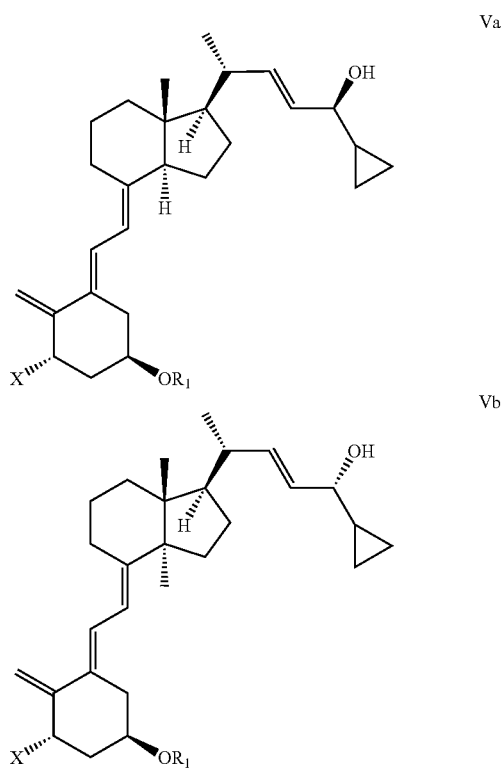

wherein X, $R_1$, and $R_2$ are as defined above.

15. A method according to claim 1, wherein X represents $OR_2$.

16. A method according to claim 15, wherein $R_1$ and/or $R_2$ represent alkylsilyl.

17. A method according to claim 15, wherein $R_1$ and/or $R_2$ represent tert-butyldimethylsilyl.

* * * * *